(12) United States Patent
Fuhrer et al.

(10) Patent No.: US 6,897,437 B2
(45) Date of Patent: May 24, 2005

(54) MOBILITY SPECTROMETER

(75) Inventors: Katrin Fuhrer, Houston, TX (US);
Kent J. Gillig, College Station, TX (US); Marc Gonin, Houston, TX (US); David H. Russell, College Station, TX (US); John A. Schultz, Houston, TX (US)

(73) Assignee: Ionwerks, Houston, TX (US)

( * ) Notice: Subject to any disclaimer, the term of this patent is extended or adjusted under 35 U.S.C. 154(b) by 308 days.

(21) Appl. No.: 09/798,030

(22) Filed: Feb. 28, 2001

(65) Prior Publication Data

US 2001/0032929 A1 Oct. 25, 2001

Related U.S. Application Data

(60) Provisional application No. 60/193,659, filed on Mar. 31, 2000, and provisional application No. 60/185,781, filed on Feb. 29, 2000.

(51) Int. Cl.$^7$ ................................................ H01J 49/40
(52) U.S. Cl. ..................................... 250/287; 250/282
(58) Field of Search ............................... 250/281, 282, 250/286, 287

(56) References Cited

U.S. PATENT DOCUMENTS

| | | | |
|---|---|---|---|
| 3,226,543 A | * 12/1965 | Melzner | |
| 3,935,452 A | * 1/1976 | Prince | 250/283 |
| 4,259,572 A | * 3/1981 | Brunnee et al. | 250/281 |
| 4,390,784 A | 6/1983 | Browning | |
| 4,855,595 A | 8/1989 | Blanchard | |
| 5,037,611 A | 8/1991 | Ledford | |
| 5,118,937 A | * 6/1992 | Hillenkamp et al. | 250/282 |
| 5,189,301 A | 2/1993 | Thekkadath | |
| 5,235,182 A | 8/1993 | Avida | |
| 5,654,545 A | 8/1997 | Holle et al. | |
| 5,736,740 A | 4/1998 | Franzen | |
| 5,789,745 A | 8/1998 | Martin et al. | |
| 5,834,771 A | * 11/1998 | Yoon et al. | 250/286 |
| 5,861,623 A | * 1/1999 | Park | 250/287 |
| 5,905,258 A | 5/1999 | Clemmer et al. | |
| 6,040,573 A | 3/2000 | Sporleder | |
| 6,040,575 A | 3/2000 | Whitehouse et al. | |
| 6,051,832 A | 4/2000 | Bradshaw | |
| 6,285,027 B1 | * 9/2001 | Chernushevich et al. | 250/287 |
| 6,323,482 B1 | * 11/2001 | Clemmer et al. | 250/287 |
| 6,331,702 B1 | * 12/2001 | Krutachinsky et al. | 250/281 |

FOREIGN PATENT DOCUMENTS

| | | |
|---|---|---|
| WO | PCT/US97/09315 | 12/1997 |
| WO | PCT/CA99/00714 | 2/2000 |
| WO | PCT/CA99/00715 | 2/2000 |
| WO | PCT/CA99/00716 | 2/2000 |
| WO | PCT/CA99/00718 | 2/2000 |

OTHER PUBLICATIONS

Phys. Rev., vol. 164, 62 (1967).
J. Am. Soc. Mass Spectrom., 7, 101–106 (1996).
Anal. Chem. 71, 4160–4165 (1999).
J. Chem. Phys., vol. 53, 11 4295–4302 (1970).
Phys. Rev. Letters, vol. 6, 3 110–111 (1961).
43$^{rd}$ ASMS Conference, p. 126.
44$^{th}$ ASMS Conference, p. 1168.
The Mobility and Diffusion of Ions in Gases, pp. 68–72, J. Wiley & Sons, 1973.

* cited by examiner

*Primary Examiner*—Jack I. Berrman
(74) *Attorney, Agent, or Firm*—Fulbright & Jaworski LLP

(57) ABSTRACT

The present invention relates to an improved ion mobility spectrometer and method for the analysis of chemical samples. The improvements are realized in the optimization of resolution and sensitivity. Increases in sensitivity are realized by preserving a narrow spatial distribution of migrating ions through the use of periodic/hyperbolic field focusing. Additionally, novel combinations and configurations of components are used to simultaneously maintain a well defined ion packet and preserve sample throughput to the detector.

106 Claims, 21 Drawing Sheets

Figure a
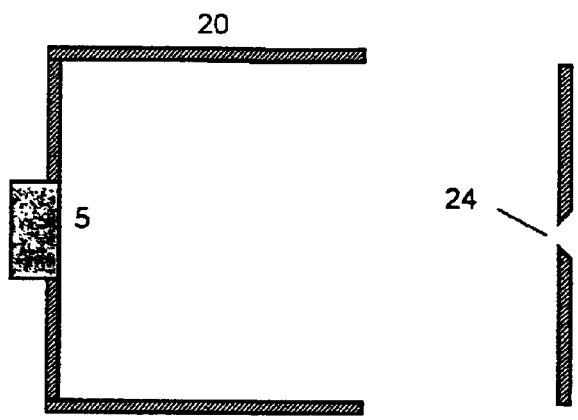
Figure b
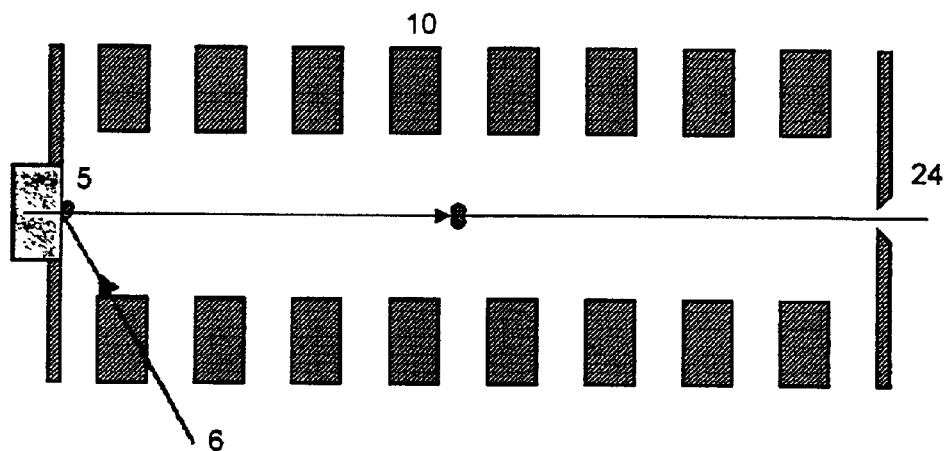
Figure 2(a) is prior art,
Figure 2(b) is simultaneously filed patent Figure a
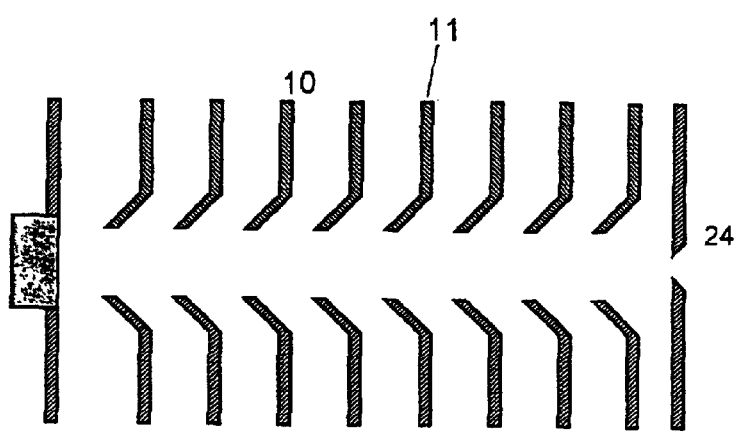
Figure b
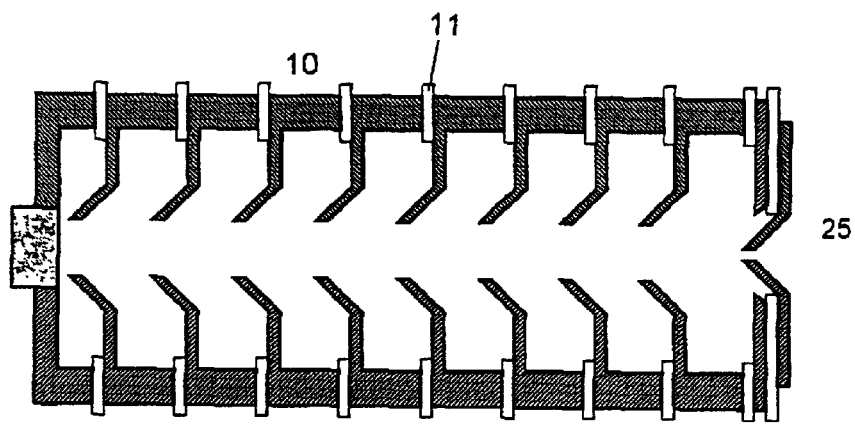
Figure 6

Figure c
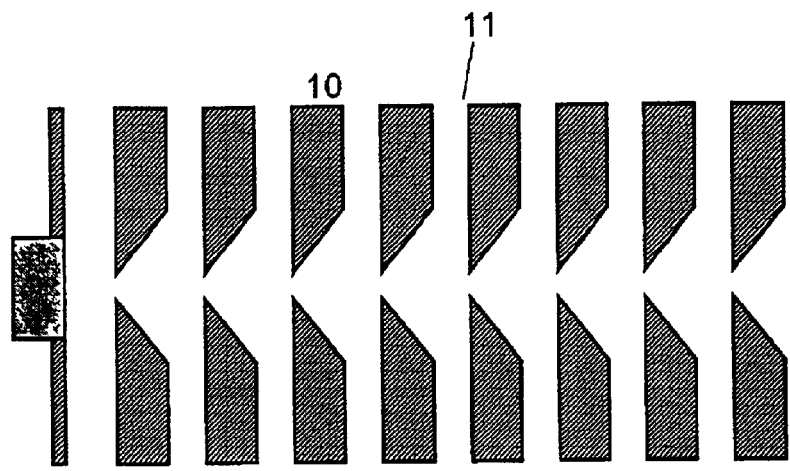
Figure d
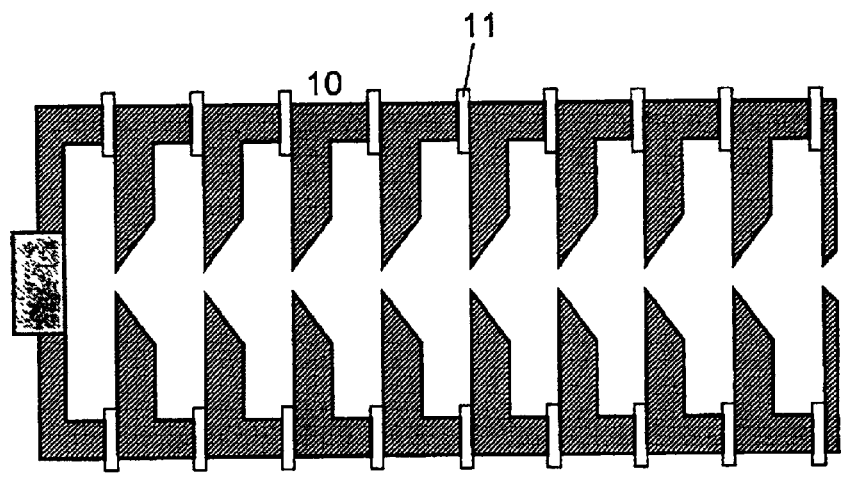
Figure 7

Figure a
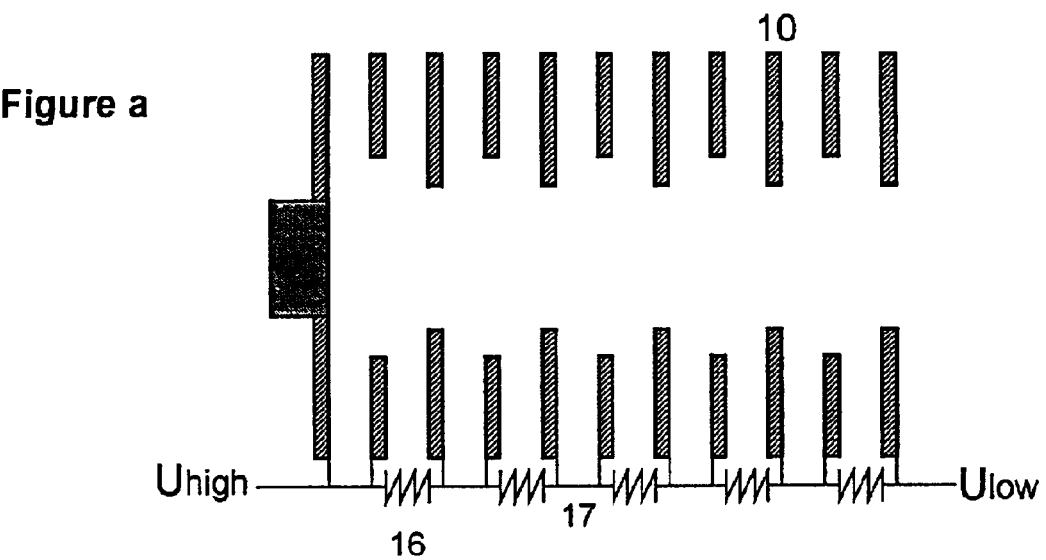
Figure b
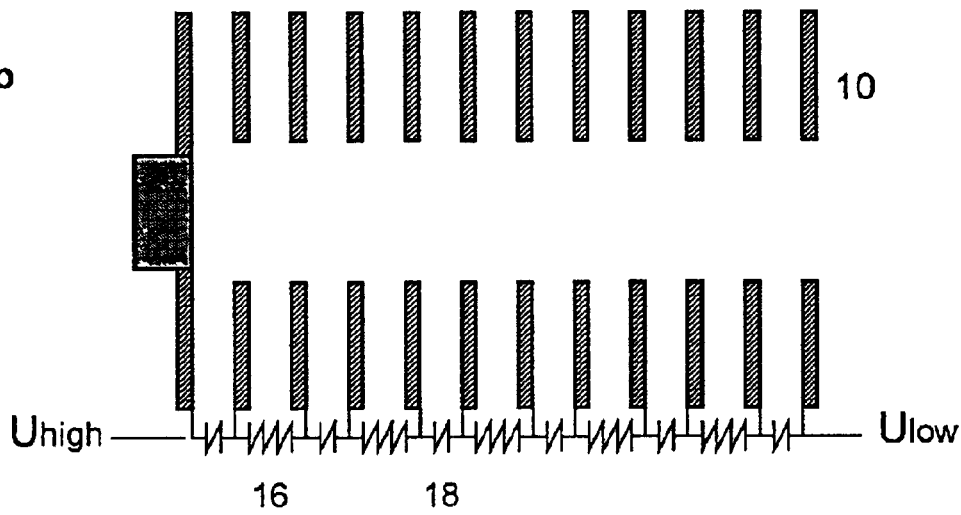
Figure 8

Figure a
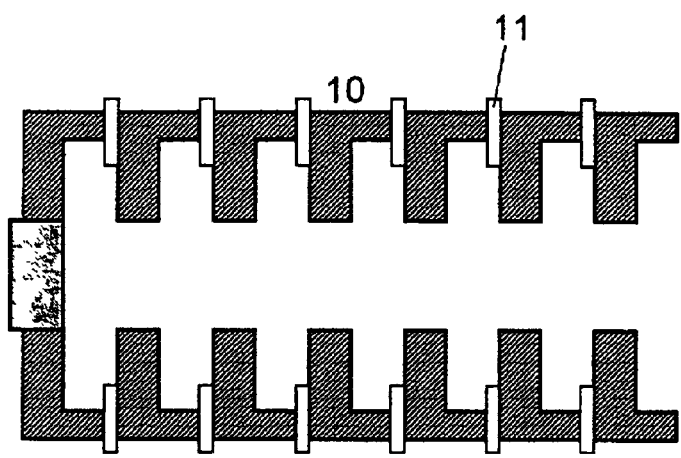
Figure b
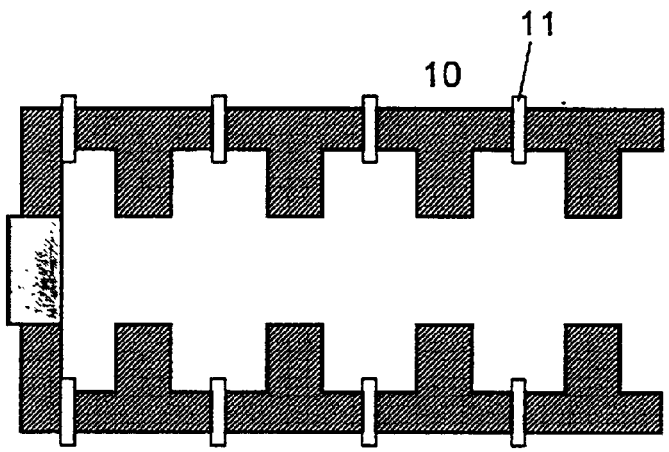
Figure 10

|  | BSA | LYS | CYC | HBB | HBA | TOTAL |
|---|---|---|---|---|---|---|
| Fragments observed | 50% / 10% | 40% / 2.4% | 53% / 20% | 28% / 3.3% | 21% / 4.3% | 41% / 8.2% |
| R Terminated Frag. Obs. | 55% / 21% | 43% / 3.6% | 60% / 60% | 38% / 6.3% | 20% / 20% | 45% / 16% |
| K Terminated Frag. Obs. | 48% / 5.3% | 36% / 0% | 52% / 16% | 24% / 0% | 22% / 0% | 40% / 5.2% |
| % AA Coverage | 69% / 20% | 89% / 4.8% | 100% / 61% | 87% / 14% | 52% / 11% | 75% / 20% |

XX% represents the present invention

Unblocked XX% represents the high vacuum mass spectrometer

MOBILITY SPECTROMETER

This application claims priority to U.S. Provisional Application No. 60/193,659, filed Mar. 31, 2000, and to U.S. Provisional Application No. 60/185,781, filed Feb. 29, 2000.

The technology was developed with government support (NSF Reference No. CHE 9629966). The government may have certain rights in the invention.

FIELD OF THE INVENTION

The present invention relates generally to instrumentation and methodology for characterization of chemical samples based on improved ion mobility spectrometry (IMS) instrumentation. The improvements are also incorporated into a mobility-mass spectrometer, which is a tandem configuration of an ion mobility spectrometer (IMS) and a mass spectrometer (MS). This apparatus is an instrument for qualitative and/or quantitative chemical and biological analysis.

BACKGROUND OF THE INVENTION

An ion mobility spectrometer is typically composed of an ionization source, a drift cell, and an ion detector, e.g. a sampling plate, an electron multiplier, or a mass spectrometer. Ion mobility spectrometry separates ions in terms of their mobility with reference to a drift/buffer gas measuring the equilibrium velocity which ions obtain. When gaseous ions in the presence of a drift gas experience a constant electric field, they accelerate until a collision occurs with a neutral molecule. This acceleration and collision sequence is repeated continuously. Over time, this scenario averages out over the macroscopic dimensions of the drift tube to a constant ion velocity based upon ion size, charge and drift gas pressure. The ratio of the velocity of a given ion to the magnitude of the electric field experienced by it is the ion mobility. In other words, the ion drift velocity ($v_d$) is inversely proportional to the electric field strength (E) where the ion mobility $K=v_d/E$ is a function of the ion volume/charge ratio. Thus IMS is a technique similar to mass spectrometry, having a separations component to it. IMS is generally characterized as having high sensitivity with moderate separation power. Separation efficiency is compromised when "bands" of the various ions spread apart as opposed to remaining together in a tight, well-defined plug. Thus, the quality of the electric field maintained in the drift cell is critical to preserving and perhaps improving separation efficiency; i.e., resolution.

Prior art instruments employ various methods to obtain a linear electric field including utilizing: 1) a series of equally spaced rings connected through a resistor chain, 2) a tube coated with a resistive material in U.S. Pat. No. 4,390,784 to Browning et al., or 3) by a more complex method such as a printed circuit board assembly drift tube in U.S. Pat. No. 6,051,832 and PCT WO 98/08087 to Bradshaw.

The combination of an ion mobility spectrometer (IMS) with a mass spectrometer (MS) has been known for a long time. In 1961 Barnes et al. were among the first to combine these two separation methods. Such instruments allow for separation and analysis of ions according to their mobility and their mass, which is often referred to as an two dimensional separation or two dimensional analysis. Young et al. realized that a time-of-flight mass spectrometer (TOFMS) is the most preferred mass spectrometer type to be used in such a combination because its ability to detect simultaneously and very rapidly (e.g. with a high scan rate) all masses emerging from the mobility spectrometer. Their combination of a mobility spectrometer with a TOFMS, in the following referred to as a Mobility-TOFMS, is shown in FIG. 1. FIG. 1 illustrates means for ion generation (1), a mobility drift cell (2), a TOFMS (3), and a small orifice (24) for ion transmission from the mobility cell to the TOFMS in this prior art instrument.

Use of MS as a detector allows for resolution based on mass-to-charge ratio after separation based upon ion mobility. Other prior art instruments and methods using sequential IMS/MS analysis have been described (see, e.g., McKight, et al. *Phys. Rev.*, 1967, 164, 62; Young, et al., *J. Chem. Phys.*, 1970, 53, 4295; U.S. Pat. No. 5,905,258 of Clemmer et al.; PCT WO 00/08456 of Guevremont) but none combine the instrumental improvements disclosed presently. When coupled with the soft ionization techniques and the sensitivity improvements realizable through use of the drift cell systems herein disclosed, the IMS/MS systems and the corresponding analytical methods of the present invention offer analytical advantages over the prior art, particularly for the analysis of macromolecular species, such as biomolecules. Shoff and Harden pioneered the use of Mobility-MS in a mode similar to tandem mass spectrometry (MS/MS). In this mode, the mobility spectrometer is used to isolate a parent ion and the mass spectrometer is used for the analysis of fragment ions (also called daughter ions) which are produced by fragmentation of the parent ions. In the following this specific technique of operating a Mobility-MS is referred to as Mobility/MS, or as Mobility/TOF if the mass spectrometer is a TOFMS-type instrument.

The challenging issue when building a Mobility-MS is achieving a high ion transmission from the mobility region into the MS region of the tandem instrument. It is at this interface that the earlier goals of ion mobility technology of using a linear field appear incongruous with the goal of maximizing ion throughput across the IMS/MS interface. The mobility section is operating at a pressure of typically between 1 mTorr and 1000 Torr whereas the MS is typically operating at pressures bellow $10^{-4}$ Torr. In order to maintain this differential pressure it is necessary to restrict the cross section of the opening that permits the ions to transfer from the mobility section to the MS section. Typically these opening cross section is well below 1 mm$^2$. Hence it is desirable to focus the ions into a narrow spatial distribution before this transmission occurs.

As discussed above, in the early development of IMS, it was believed that the use of focusing methods (i.e., non-linear fields) was detrimental because it was believed that such focusing methods would deteriorate the resolution of the mobility spectrometer. Also, many of the early mobility spectrometers were used to investigate the mobility constant of ions, in which case it is preferable to use a homogeneous field of known value along the ion drift path. Therefore, most instruments just used a large area ion detector at the end of the mobility drift and ion focusing was not an overarching concern. It was only when the need for compact and sensitive IMS emerged when the focusing of the drift ions was addressed.

In 1989, in U.S. Pat. No. 4,855,595, Blanchard taught a focusing method based on time-varying electric fields.

In 1992, Avida et al. U.S. Pat. No. 5,235,182 found that inhomogeneous fringe fields along the mobility drift cell could be used to reduce the loss of ions from the edge of the mobility drift cell and hence to reduce the size of mobility instruments. The inhomogeneous fringe fields were generated by simply increasing the thickness of the field-generating ring electrodes such that the ratio of electrode thickness to inter-electrode gap could be manipulated to provide the fringe fields.

In 1993 Thekkadath (U.S. Pat. No. 5,189,301) taught a cup shaped electrode to generate a focusing field. This field configuration compares to the Vehnelt cylinder used in non-collisional ion optics.

In 1996 Gillig et al. published a magnetic field to confine the ions in a small beam in order to increase the ion transmission from the mobility section into a mass spectrometer.

In 1999 Gillig used a periodic configuration of focusing and defocusing fields in order to increase the ion transmission from the mobility section into the MS section, as discussed above. This field configuration compares to a technique used in non-collisional ion optics where series of focusing and defocusing lenses are used to confine ion beams in large ion accelerators [Septier, p. 360].

Nonlinear electric fields have also been introduced to ion mobility drift cells to focus ions to a detector as presented in U.S. Pat. No. 5,189,301 to Thekkadath utilizing a cup electrode and U.S. Pat. No. 4,855,595 to Blanchard using nonlinear fields for the purpose of controlling ions, trapping ions in a potential well to normalize drift differences and increase sensitivity. All of these methods have drawbacks associated with their construction and ease of implementation. Therefore, it is the object of this invention to reduce or eliminate disadvantages and problems associated with prior art ion mobility instruments.

Additionally, improvements at the drift tube/MS interface are described. The use of radio frequency focusing using rf quadrupoles, the use of microchannel aperture plates, and the pre-selection of parent ions for mass analysis by collision-, surface-, or photo-induced dissociation is described. Use of these methods in the instrumental platforms and the corresponding analytical methods represents a further improvement afforded by the invention over the prior art.

SUMMARY OF THE INVENTION

In a specific embodiment of the present invention there is are methods and apparatuses for separating and analyzing ions comprising an ionization source to generate ions, an ion drift cell coupled to said ionization source, in which the ions are separated according to their mobility and which comprises electrodes for transporting and focusing the ions, the focusing uses a superposition of periodic field focusing and hyperbolic field focusing. A detector is coupled to the ion drift cell for detection of the ions.

In a closely related embodiment, instead of separating and analyzing the ions, the invention may be used as an ion transport instrument, useful in any application where the transport of ions for an ion source to a desired location is required.

In another embodiment, of the present invention there are methods and apparatuses for separating and analyzing ions comprising an ionization source to generate ions, an ion drift cell coupled to said ionization source, in which the ions are separated according to their mobility and which comprises electrodes for transporting and focusing the ions, the focusing uses a combination of periodic field focusing and hyperbolic field focusing. A detector is coupled to the ion drift cell for detection of the ions. Preferably, this combination is a sequential combination of the fields.

In a closely related embodiment, instead of separating and analyzing the ions, the invention may be used as an ion transport instrument, useful in any application where the transport of ions for an ion source to a desired location is required.

In a further embodiment, methods and apparatuses analogous to those described above utilize purely hyperbolic field focusing. These embodiments use sliding tube electrodes and hyperbolic-shaped electrodes.

In specific embodiments of the separation and analysis methods and apparatuses described above, the detector may be a mass spectrometer, preferably a time-of-flight mass spectrometer (TOFMS), and more preferably, a TOFMS having a flight tube positioned orthogonally with respect to the ion mobility drift tube cell. In other embodiments, there are specific interfaces between the mass spectrometer and the drift cell. These include known interfaces, such as microchannel aperture plates and radio frequency focusing interfaces. For microchannel aperture plates, the preferred embodiment uses a bundle of capillaries. The radio frequency interface may be a combination of a radio frequency electric field and a direct current electric field. Other embodiments use known fragmentation means for fragmenting ions after mobility separation and before mass analysis. These include collision-induced dissociation (CID), surface-induced dissociation (SID), and electron impact dissociation or a combination thereof Alternatively, there may be a radio frequency quadrupole to focus the ions after fragmentation.

Specific embodiments use electrodes of a variety of configurations and conformations. Cone-shaped (conical) electrodes, thick plate electrodes with holes, cup-shaped electrodes are examples of some embodiments. In one specific embodiment of electrodes with holes, multiple holes are used in order to focus several parallel beams of ions, thereby resulting in "multi-channel" ion mobility. The electrodes may be arranged in a variety of ways. They may have equal or unequal distance between them, they may have equal or unequal hole diameters, and they may have unequal potentials applied to them. An electrode stack is used in one embodiment; preferably this stack contains seal rings, positioning rings and/or positioning tubes that act to position the electrodes or seal the drift chamber.

The above-described embodiments possess further specific embodiments related to the ionizing beam and it associated devices. Preferably, the ionizing beam is a laser, but it may be any known, useful ionization source. In one embodiment, one or more mirrors are used to redirect the ionizing beam to the sample to be ionized. This allows flexibility in the positioning of the ionization source. A number of embodiments use different sample holders which contain the sample for ionization. A rotatable sample holder for sequential sample ionization is another embodiment. Alternatively, a moving belt sample holder may be used. Preferably, the sample holder is positioned orthogonally to the drift cell axis.

The invention described herein has the goal of improving the general instrumental design and, as a result, the analytical performance of ion mobility instruments. This aspect of the present invention is focused on enhanced analytical performance, which results from using the improvements in the components of the instrumentation. These improvements primarily lie in the various electrode configurations and conformations. In a specific embodiment of the present invention, an apparatus and method for performing ion mobility spectrometry uses an ionization source, a drift cell and a detector. It also uses a parallel electrode assembly comprising a component of at least one field correcting ring electrode or at least one movable cylindrical electrode or at least one radius of curvature electrode. Preferably, matrix-assisted laser desorption ionization is used to ionize samples. Alternatively, electrospray ionization, a laser ionization, a photoionization, electron ionization, chemical ionization, an electric field ionization, surface ionization, radioactive ionization, discharge ionization and/or a multiphoton ionization may be used to ionize sample.

In a specific embodiment, a mass spectrometer is used as a detector and preferably it is a TOFMS and more preferably, it is a TOFMS having a flight tube positioned orthogonally with respect to the drift tube of the ion mobility cell. Alternatively, an IMS detector consisting of an ion collector and an amplifier may be used. In the TOFMS embodiment, TOFMS ion sources may include surface-induced ionization, collision-induced ionization, or photo-induced ionization. The interface between the drift cell and the mass spectrometer may be, for example, a microchannel plate aperture or a radio frequency focusing interface. In the preferred radio frequency focusing embodiment, the interface uses a combination of a radio frequency electric field and a direct current electric field. In the preferred microchannel aperture plate embodiment, a bundle of capillaries is used.

BRIEF DESCRIPTION OF THE DRAWINGS

FIG. 2(a) is a prior art ion mobility spectrometer. FIG. 2(b) is a periodic field focusing device with thick rings described in the simultaneously filed application which is incorporated by reference herein.

FIG. 6(a): Instrumental embodiment incorporating a superposition of hyperbolic field focussing and periodic field focussing with cone shaped electrodes.

FIG. 6(b): Sealed version of the mobility drift cell of FIG. 6(a).

FIG. 7(a): Embodiment incorporating superposition of hyperbolic focusing and periodic field focusing with cone shaped holes in thick plates.

FIG. 7(b): Sealed version of the mobility drift cell of FIG. 7(a).

FIG. 8(a): Embodiment using pairs of thin electrode plates in which the electrodes forming the pair have unequal hole diameter.

FIG. 8(b): Similar to FIG. 8(a) differing in that the holes of each pair are equal.

FIG. 10(a): Embodiment using the superposition of periodic field focusing and hyperbolic field focusing.

FIG. 10(b): Purely periodic (non-hyperbolic) field focusing analog of FIG. 10(a).

DETAILED DESCRIPTION OF THE INVENTION

Figure 1:
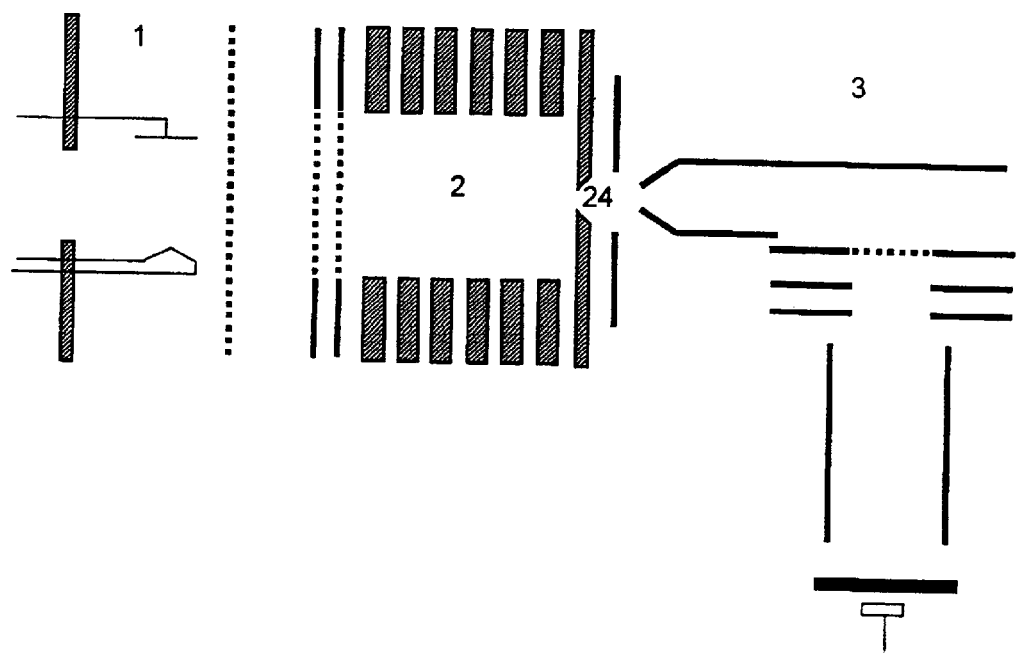
FIG. 1: Prior art Mobility-TOFMS as published by Young et al.

As used herein, "drift tube diameter" is defined as the distance from the spectrometer axis to the electrode surface nearest to the spectrometer axis. In the case of multiple coaxial series of electrodes, this distance refers to that from the spectrometer axis to the electrode surface nearest to the spectrometer axis of the innermost coaxial series of electrodes. It is synonymous with the expression "inner diameter".

As used herein, a "combination" of periodic field focussing and hyperbolic field focusing in an ion drift cell is any coexistence of the two types of fields in the drift cell; they may be sequential to one another (i.e., serial; and in any order) or be superimposed (i.e., a superposition) on one another. It may also include multiple field regions in the drift cell. It may also include one or more regions of a superposition and one or more other regions of a sequential combination.

As used herein, "electrode width" is defined as the ratio of the length, L, of the drift region to the total number, N, of periods in the drift region minus the inter-electrode gap width, G; alternatively, it is mathematically defined as (L/N)−G.

As used herein, "focusing", when used in reference to a beam of ions, is defined as any imaging event that reduces the spread of the ion beam to any degree; it does not necessarily require that the reduction result in a focus point.

As used herein, "gaps of a metal helix" are the distances between the wire or wire-like structures which make up the metal helix.

As used herein, a "heterogeneous electric field", or alternatively, an "electric field exhibiting substantial heterogeneity" is an electric field in which the deviation from a linear electric field along the spectrometer axis at each electrode or electrode gap is greater than 0.10%.

As used herein, a "homogeneous electric field", or alternatively, an "electric field exhibiting substantial homogeneity" is an electric field in which the maximum deviation from a linear electric field along the spectrometer axis at each electrode or electrode gap is no more than 0.10%.

As used herein, "hyperbolic focusing field" for an ion drift cell is defined as a field characterized by nonlinear equipotential lines and further characterized by an asymmetry of the nonlinear equipotential lines along the axis of the spectrometer.

As used herein, the abbreviation "IMS" is defined as ion mobility spectrometry.

As used herein, "inter-electrode gap" is defined as any distance between electrodes that does not consist of an electrode; this may, for example, be an insulating material or air.

As used herein, "inter-electrode gap width" is defined as the distance between adjacent coaxial electrodes within a series.

As used herein, MALDI is defined as matrix assisted laser desorption ionization.

As used herein, the abbreviation "MS" is defined as mass spectrometry.

As used herein, "period" is defined as an electrode at a unique potential. N is the "number of periods for a given drift tube length" and is the number of electrodes having unique potentials.

As used herein, the expression "periodic focusing field" for an ion drift cell is defined as an electric field characterized by alternating periods of substantial homogeneity and substantial heterogeneity in which the regions of substantial heterogeneity as measured by % ($\Delta V/V$) is greater than about 0.1.

As used herein, "potential" means an electrical potential or synonymously, a voltage.

As used herein, "resistively coated metal helixes" are continuous metal wires or wire-like structures coated with any resistive material, generally taking the shape of a coil.

As used herein, a "sequential" hyperbolic field and periodic field refers to a specific combination of the two fields characterized by distinct regions of either field without substantial overlap with the other field; the order (i.e., periodic followed by hyperbolic or vice versa) is unspecified without more. It is synonymous with a "sequential combination".

As used herein, the term "spectrometer axis" is defined as the major (lengthwise) axis of the spectrometer. This applies herein to both ion mobility instruments and mass spectrometric instruments.

As used herein, a "superposition" of a hyperbolic field and a periodic field refers to a specific combination of the two fields characterized by overlap of the two fields (i.e., the two fields are superimposed on one another) resulting in an overall resultant field.

As used herein, the abbreviation "TOFMS" is defined as time-of-flight mass spectrometry.

As used herein, a "unit helix thickness" is the width of the wire or wire-like structure of a resistively coated metal helix.

% ($\Delta V/V$) is defined as the percentage deviation from a linear electric field along the spectrometer axis at each electrode or electrode gap.

Hyperbolic Field Focusing

Figure 3:
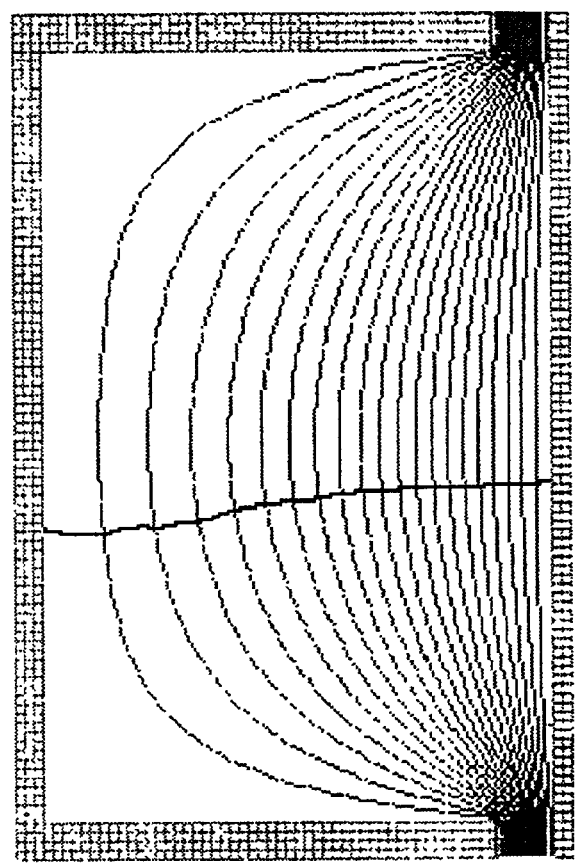
FIG. 3: Field lines in a drift tube of a hyperbolic (nonperiodic) instrument.

Hyperbolic focusing takes advantage of the fact that ions in gases follow very closely a path that is always perpendicular to the equipotential surfaces. Here, we address the focussing of ion beams in gases using concave electric fields as hyperbolic field focussing. This type of focussing was used in mobility cells as taught by Thekkadath in U.S. Pat. No. 5,189,301 by using a cup shaped electrode. Blanchard, U.S. Pat. No. 4,855,595 used also a hyperbolic field focussing method with time varying fields. FIG. 2(a) illustrates a configuration for using hyperbolic field focusing similar to the one claimed by Thekkadath. A fixed, single cup shaped electrode (20) generates a hyperbolic-like field close to the center axis. Ions are sourced at (5) and sampled at aperture (24). The field lines of such a configuration and the simulated path of an ion in this field are illustrated in FIG. 3. The salient feature of the field of FIG. 3 is that is everywhere both nonlinear and asymmetrical. The distortions from linearity extend in one direction only. Importantly, in the prior art disclosing hyperbolic fields, there are no discrete regions of one or more distinct sub-fields of any kind (i.e., linear fields, non-linear/symmetric fields, or different non-linear/asymmetric fields) within the drift cell. The fields are uniform within the drift cell; they are everywhere hyperbolic within the drift cell; there are no discrete regions of having different resultant fields. Referring back to the electrode configuration of FIG. 2(a) that is responsible for the field lines of FIG. 3, it should be noted that although the cup-shaped geometry is symmetrical, it is arranged (i.e., juxtaposed) around the drift cell in a asymmetrical fashion in that the electrode structure does not extend to the axis defining the aperture plate. In general, a source of asymmetry in the field-generating component (electrode) is required. This can come from the configuration of one or more electrodes with respect to the drift cell and/or to one another (e.g., asymmetrically arranged electrode(s); in which the component electrode(s) may have either individual symmetry or asymmetry). It may also be introduced from the conformation of the individual electrodes in a series (e.g., a symmetrical arrangement of electrodes having individual asymmetry, or an asymmetrical arrangement of individually symmetric electrodes, or some combination thereof). Other variations are possible while still achieving a hyperbolic field. The general requirement is a fixed configuration and conformation of electrode(s) about the drift tube such that only one resultant field in the drift tube results, and the fixed configuration and conformation must somewhere contain an inherent asymmetry.

Periodic Field Focusing

Figure 4:
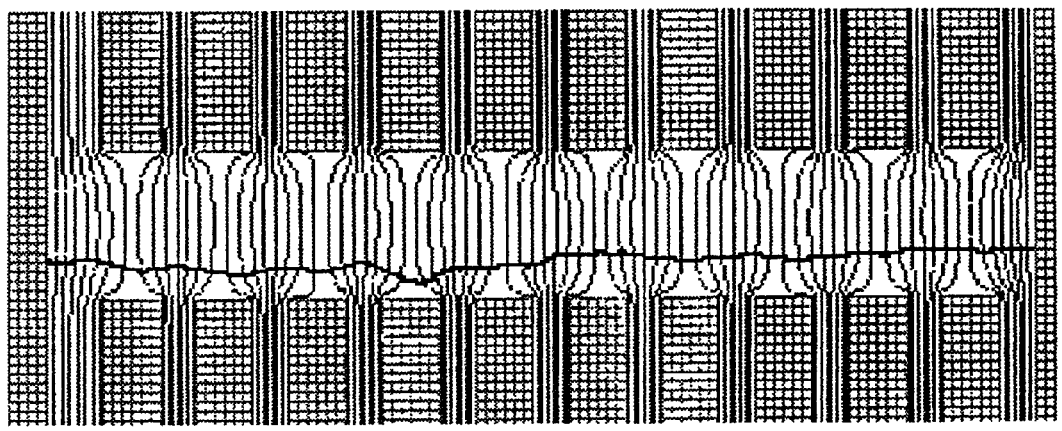
FIG. 4: Field lines in a drift tube of the periodic instrument described in the application simultaneously filed and incorporated by reference herein.

The focusing of ion beams in gases with periodic fields is described in more detail in a patent application simultaneously filed with this one, having Ser. No. 09/798,032, and now issued as U.S. Pat. No. 6,639,213 and incorporated by reference herein. FIG. 2(b) illustrates a mobility drift cell with periodic field focussing taught in said reference. Ions are sourced at 5 and migrate in the drift tube under the influence of a field created by ring electrodes 10 and are sampled at aperture 24. In the embodiment of FIG. 2(b) and external excitation source 6 is used for ionization. The electric field of such a configuration and the path of an ion in this field is illustrated in FIG. 4. The basic functioning principle is as follows. Off-axis ions feel a periodically changing electric field with focusing and defocusing properties. After drifting in a focusing portion of the field, the ion will enter a defocusing portion of the field. However, since the ions will enter the defocusing field at a distance closer to the axis as it entered the focusing field, the defocusing effect will be smaller than the focusing effect previously experienced. Hence, during the path of the ion in the device of FIG. 2(b), the focusing properties will dominate and compensate the defocusing effects of the diffusion.

Figure 5:
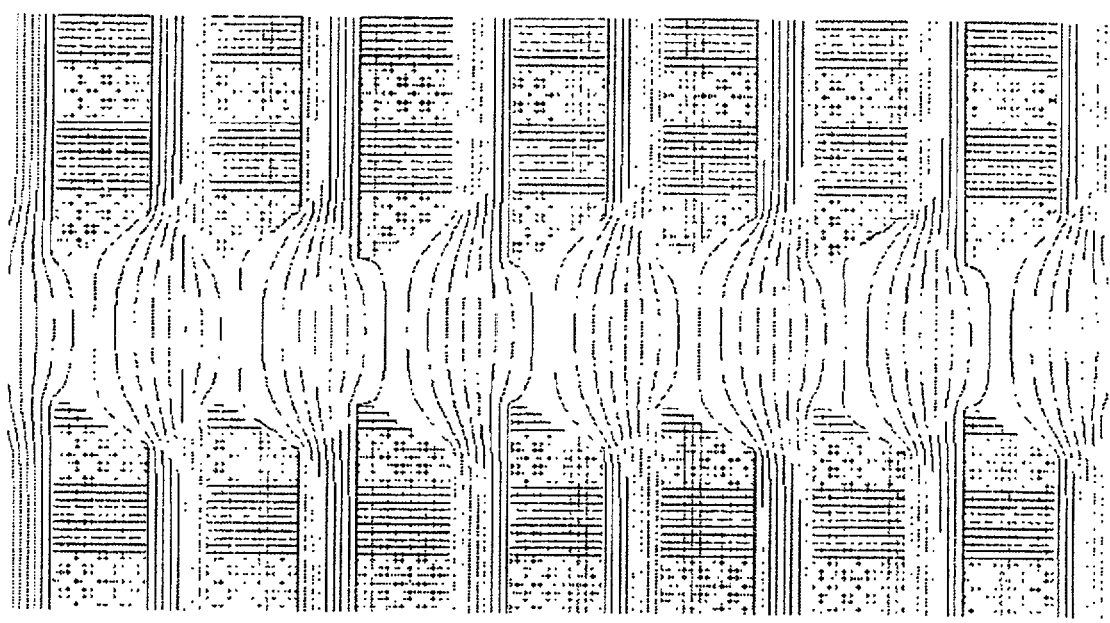
FIG. 5: Field lines in a drift tube of a periodic hyperbolic instrument.

Embodiments with Combined Periodic and Hyperbolic Focusing Fields and Novel (Purely) Hyperbolic Focusing Fields We found that combining and superimposing both methods yields the best results, according to our simulations. Our embodiments allow building mobility drift cells having the optimum trade-off between mobility resolving power and ion beam focusing. For example, in a Mobility-MS with limited pumping speed, the cross section of the ion transmission channel from the mobility section to the MS has to be reduced in order to maintain the pressure differentials. In order to maintain acceptable sensitivity, it may be necessary to increase ion focusing in the mobility cell, trading off some of the mobility resolving power. Our simulations show that superimposing hyperbolic field focussing and periodic field focussing helps to minimize the trade off. FIG. 5 illustrates the field lines in the drift cell for a periodic hyperbolic field instrument.

Cone shaped electrodes as in FIG. 6(a) allow for a maximum portion of hyperbolic focussing in the superposition of the two focussing methods. A series of cone shaped electrodes 11 form a drift tube 10 which terminates at ion aperture 24. This yields good properties but the electrodes are rather expensive to produce. FIG. 6(b) shows an embodiment with the same ion optical properties but having electrodes 10 that are isolated from each other with a foil or with a thin insulating material 11 that can at the same time also serve as the sealing the interior of the mobility drift cell from the exterior region. The thin insulating materials may be, for example, kapton film or teflon sheets. Such sealing is often required in order to maintain pressure difference or in order to maintain the gas purity in the interior of the cell. Ions are sampled at aperture 25.

A simpler and less expensive embodiment is using beveled thick plate electrodes resulting in cone shaped holes along the spectrometer axis is shown in FIG. 7. The cone angles angle in FIG. 7 are approximately 90 degrees, but changing this angle allows for adjusting the portion of periodic field focusing and hyperbolic field focusing. In the extreme case of a cone angle of 0 degrees, one would obtain the embodiment for pure periodic field focussing described by Gillig.

FIG. 8(a) teaches an embodiment which uses an even more simple geometry with thin electrode plates 10. Pairs of the plates are electrically connected 17 by resistors 16 which determine the potential of each pair, allowing for the use of unequal potential differences between electrodes. The two electrodes forming one pair preferably have an unequal hole diameter. The difference in this diameter determines the portion of periodic field focusing and hyperbolic field focusing. In one extreme, when the hole diameters are equal, one obtains pure periodic field focussing. Alternatively, electrode assemblies having unequal spacing between individual electrodes may be used for the same effect.

FIG. 8(b) teaches an embodiment in which the holes of each pair are equal, but instead of shortening the pairs 17 the electrodes forming a pair are connected by resistors 18 of smaller resistance than those connecting the pairs 16. This allows to superimpose hyperbolic field focussing. In other words, the pair resistor 18 has a very low value, the embodiment will become purely periodic field focussing. In an other extreme, when the pair resistors 18 are of equal resistance as the resistors connecting the pairs 16, a purely homogeneous field without any focussing but with high resolving power will result.

Figure 9:
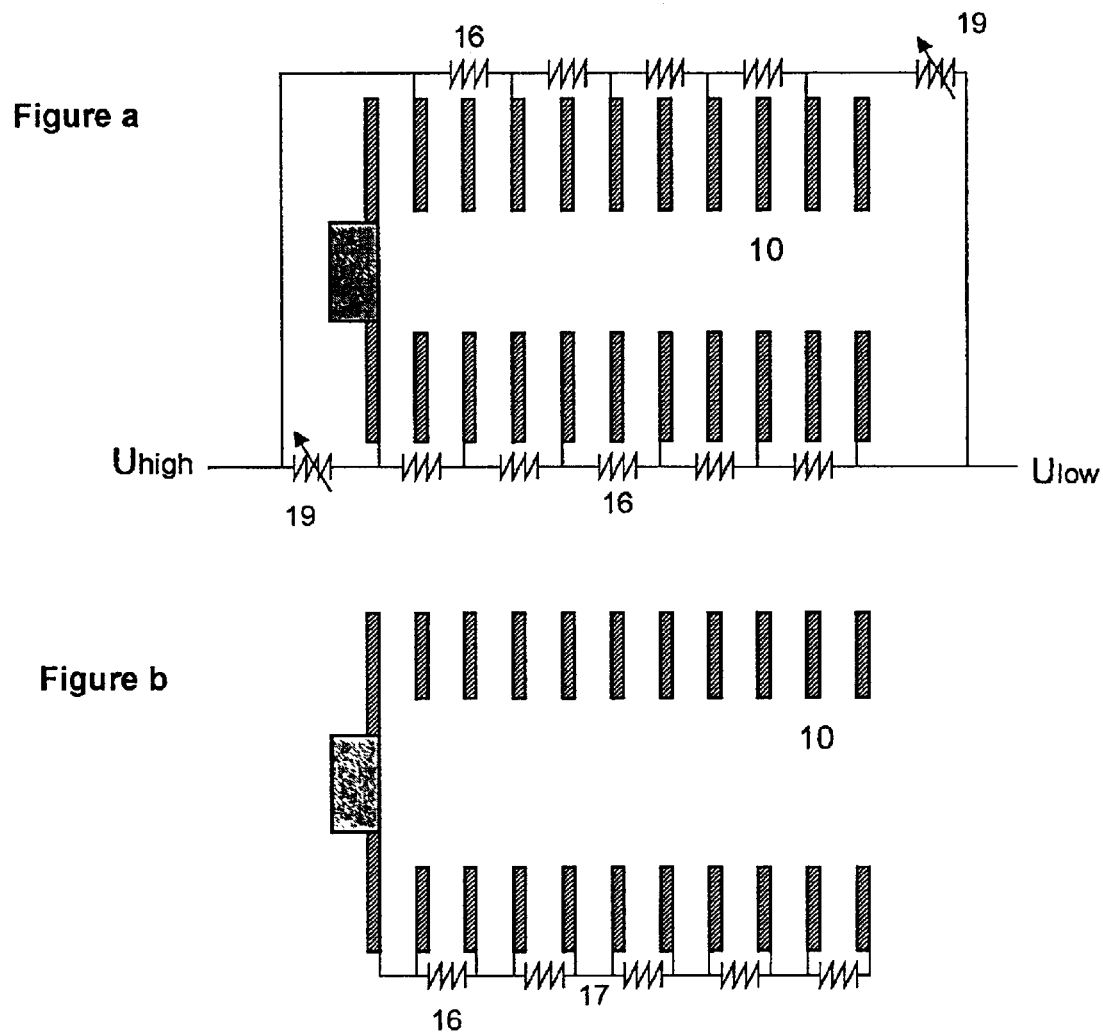
FIG. 9(a) and 9(b): Adjustable embodiment of that illustrated in FIGS. 8(a) and 8(b).

FIG. 9(a) teaches an adjustable embodiment of the concept above. Also in this embodiment, always two adjacent electrodes form a pair. However, there are two independent voltage dividers chains, which independently supply the potential of the first electrode of each pair and the second electrode of each pair respectively. The voltage dividing resistors 16 have the same resistance in both chains. Each chain, however, also incorporates an adjustable resistor 19 which preferably are adjusted to the same value. If the resistance of the adjustable resistors 19 is adjusted to zero, then both plates of each pair will have the same potential, which results in a purely periodic field focusing. The field configuration is then equal to the situation illustrated in FIG. 9(b). If the resistance of the adjustable resistors 19 is adjusted to half the value of chain resistor 16, then a essentially homogeneous field without any focusing properties will result. If the resistance of the adjustable resistors 19 is adjusted to some value in between the extreme cases just mentioned, a superposition of periodic field focussing and hyperbolic field focussing will result. This embodiment may of course be combined with the embodiment of FIG. 8(a) which uses electrode plates of different hole diameters in each pair.

FIG. 10(a) teaches an embodiment with sealed mobility drift cell and a series of cup-shaped electrodes. This embodiment uses also a superposition of periodic field focusing and hyperbolic field focusing.

FIG. 10(b) teaches a sealed embodiment of a purely periodic field focussing mobility drift cell using electrodes 10 with T-shape cross section and thin insulators 11.

Figure 11:
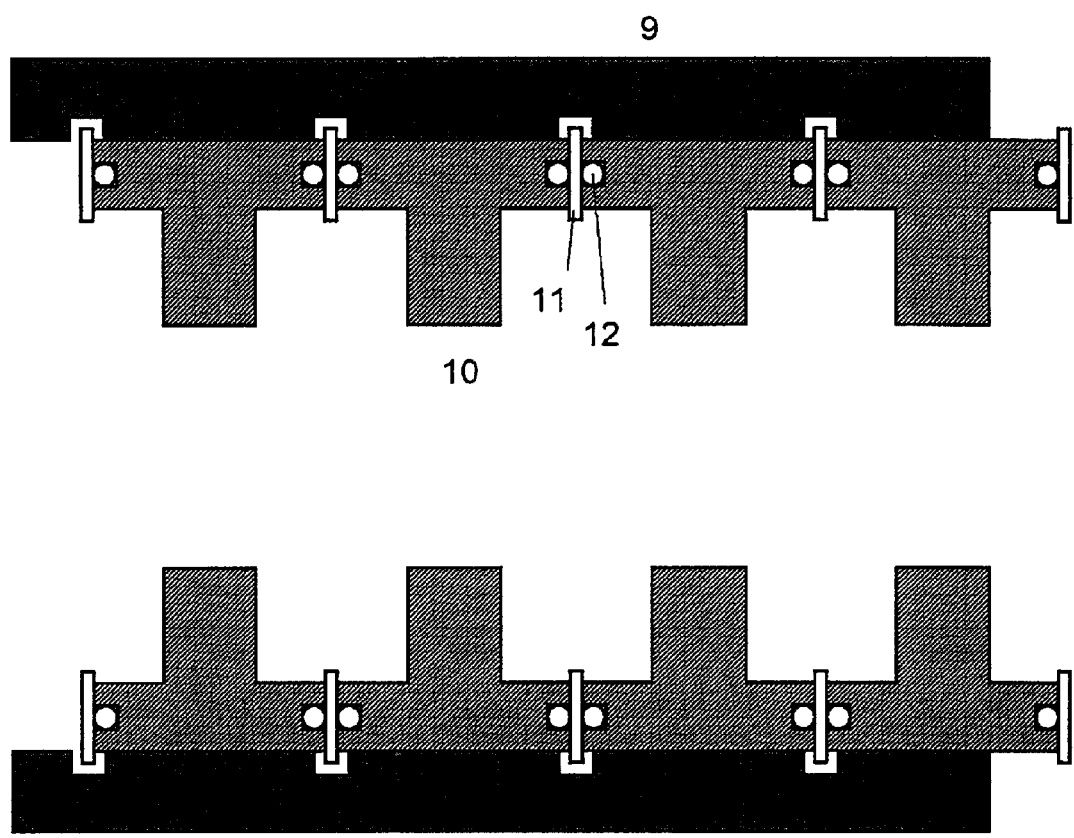
FIG. 11: Detailed illustration of insulation and sealing embodiment between in which o-rings surround the insulator gaps.
Figure 12:
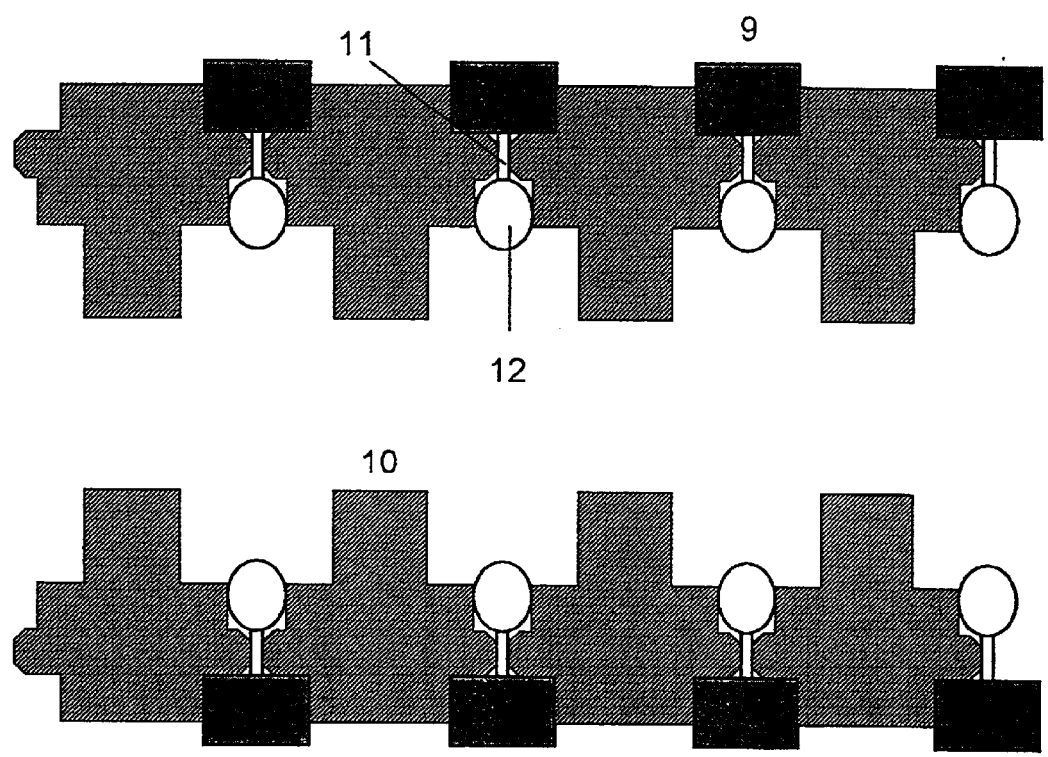
FIG. 12: Detailed illustration of insulation and sealing embodiment between in which o-rings abut the insulator gaps in the direction of the drift cell.

FIG. 11 and FIG. 12 illustrate in more detail the insulation and sealing between ring electrodes 10 which can be used in all (periodic, periodic hyperbolic, etc.) embodiments discussed so far. Insulating foils or thin plates 10 are used for electrical insulation. Seal rings 12 are used for vacuum sealing. Additional seal rings 9 may be used for positioning of the electrodes 10. Instead of such rings, a tube may be used.

Figure 13:
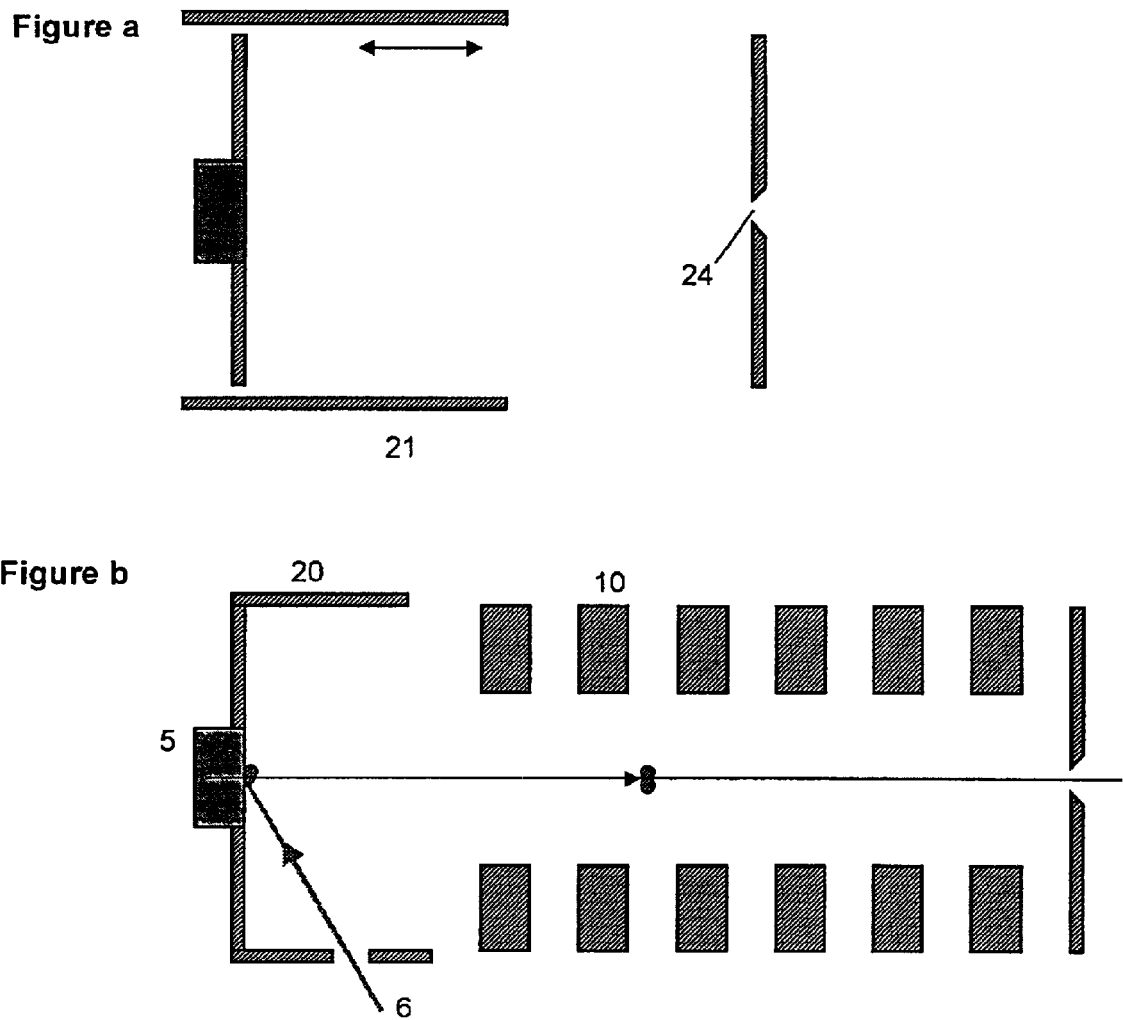
FIG. 13(a) is an instrumental embodiment capable of hyperbolic field focusing similar to the prior art instrument of 2(a) but differing in that the electrode is slidably adjustable.
FIG. 13(b) illustrates an instrument capable of serial (as opposed to superimposed) hyperbolic and periodic field focusing.

FIG. 13(a) teaches an embodiment with hyperbolic field focussing similar to the prior art embodiment in FIG. 2(a), but including a novel adjustable sliding tube electrode 21 in order to adjust the hyperbolic field inside the cup. This allows adjusting the focusing of the ion beam in respect to its transmission to the MS through the orifice 24. It also allows determining the trade-off between focussing and mobility resolving power. Another possible embodiment involves replacing the sliding tube electrode with an electrode with hyperbolic shaped geometry.

FIG. 13(b) teaches a combination of hyperbolic field focusing and periodic field focusing, but instead of superimposing the two focusing fields, the focusing methods are applied serially. Hyperbolic field focusing, accomplished through the use of fixed electrode 20, is used at the location of the pulsed ionization by laser 6 (or ion shutter for non-pulsed ionization methods), and periodic field focusing, accomplished through the use of ring electrodes 10, is applied further downstream the mobility drift cell. This embodiment can of course be combined with any other embodiment discussed so far.

Figure 14:
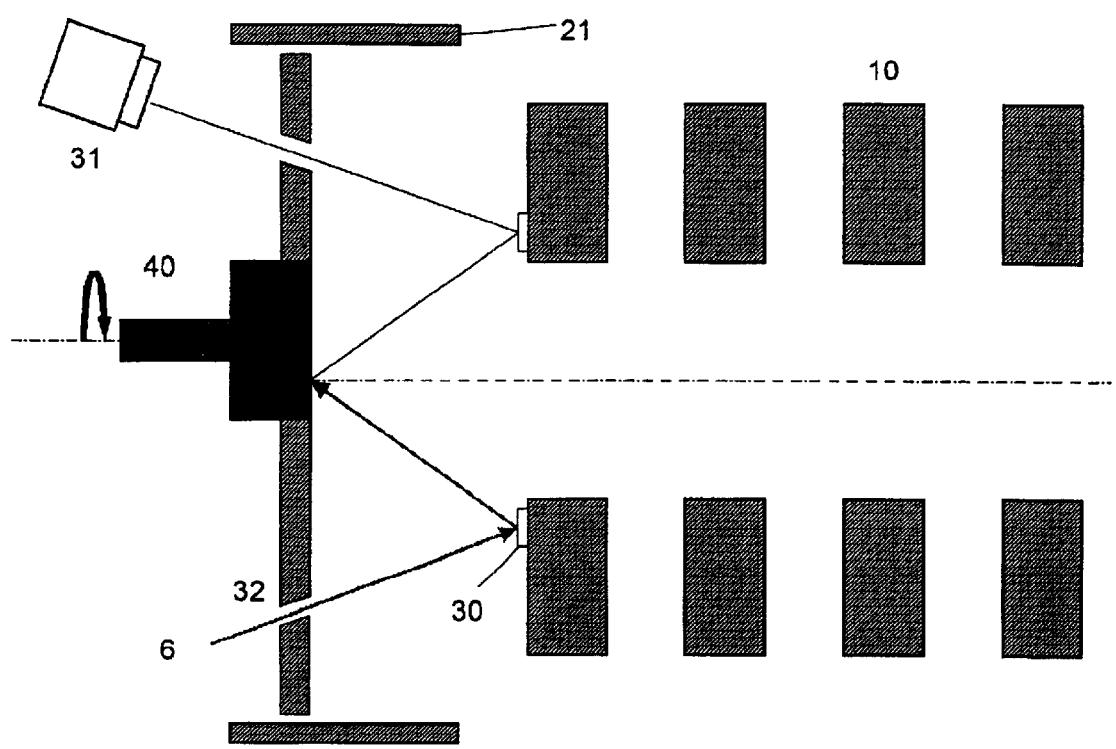
FIG. 14: Embodiment having external ionizing beam and camera a rotatable sample holder; this embodiment uses mirrors to redirect the ionizing beam to the sample.

FIG. 14 illustrates an embodiment of the ionization region with ionizing beam 6 entering through a windows 32 from behind the sample surface 5 and being redirected with a mirror 30 onto the sample. In the same way, the camera 31 serves to observe the ionization process via a mirror. A rotatable sample holder 40 allows turning several samples into the focus position of the ionizing beam 6 without removing the sample holder 40. In this way, a number of samples may be sequentially analyzed. Many mechanical design variations are possible for this embodiment, particularly those using multiple mirrors, allowing the source of the ionizing beam to be positioned in a variety of positions; e.g., it may, for example, be positioned behind the sample holding surface.

Figure 15:
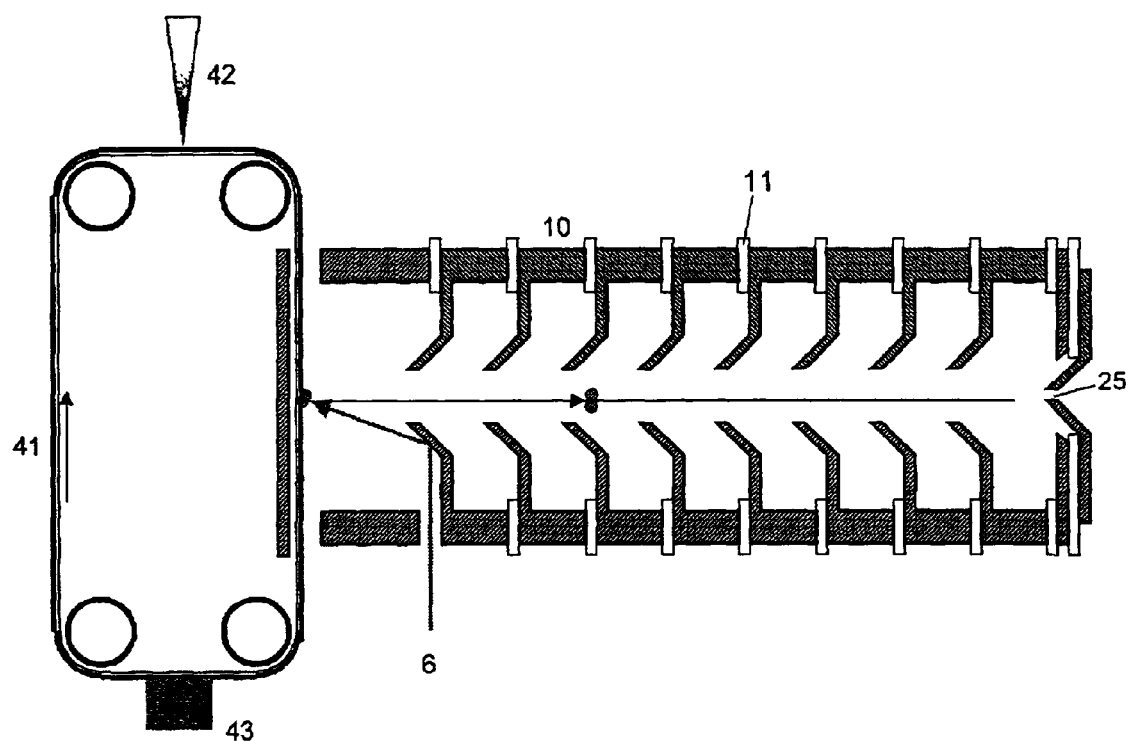
FIG. 15: Embodiment having a moving belt sample holder allowing for manual or automatic sample deposition.

In FIG. 15, an embodiment with a moving belt sample holder 41 which allows for manual or automatic sample deposition 42, sample analysis or separation by mobility cells discussed in previous figures, and sample holder cleaning 43. Ionizing beam 6, electrodes 10, insulating spacers 11 and sampling aperture 25 are also illustrated. This embodiment allows the ionizing beam to enter the drift cell essentially orthogonal to the drift cell axis. The sample holder of this embodiment allows one to sequentially expose several samples to the ionizing beam by positioning the samples at various locations on the moving belt. Rotation of the belt allows one to proceed from sample to sample for analyses. Many mechanical design variations are possible for this embodiment. For example, multiple mirrors can be used to allow for flexibility in the positioning of the source of the ionizing beam.

A number of variations on the instrumentation taught above are possible without deviating from the scope of the invention. For instance, the examples above all involve single orifice (i.e., single hole) electrodes. It is possible to utilize electrodes having multiple holes to make up the drift cell. The individual ion paths defined by these holes are different ion channels within which ion mobility can be performed. Various combinations of the electrode geometries taught above are possible. In this way, a multiple channel ion mobility instrument can be constructed. Additionally, a purely ion transport device can be constructed with the disclosed electrode geometries and configurations. Such a device can be used outside of the context of the basic ion mobility spectrometry method. For instance, such an ion transport device would find utility in any application where guiding ions from one instrument or area to another is desirable. For example, applications are possible to transfer ions from an ion source to a mass spectrometer.

Another notable advantage of using heterogeneous fields in the mobility drift cell as herein described is the increase in discharge voltage when operating the mobility cell close to the Paschen minimum. We have observed that one can apply higher voltages across the cell without causing a gas discharge.

In addition to the aforementioned to the advantages realized through the use of hyperbolic field focusing, a number of other aspects of the present invention are described below. These additional aspects of the present invention involve a number of instrumental and method refinements resulting in improved apparatuses and methods for separating and analyzing ions in a high-pressure gas. The resulting methods and apparatuses enable analyses having high sensitivity for charged species while maintaining resolution comparable to that achieved in moderate resolution drift tubes known to the art while providing an easily constructed and implemented solution. The apparatus comprises one or two electrodes to which voltages are applied, spaced apart from an aperture plate which samples charged particles. Once sampled using the aperture plate, the ions may be detected by a conventional IMS detector (consisting of an electron multiplier and associated electronics) or a mass spectrometer.

Ions can be produced by any number of means including in part electrospray ionization, laser ionization, photoionization, electron ionization, chemical ionization, electric field ionization, surface ionization, radioactive ionization, discharge ionization, multiphoton ionization, etc., with the chosen method of ionization being matrix assisted laser desorption ionization (MALDI). The laser is the preferred example of an ionizing beam excitation. In one embodiment of the invention ions are produced by MALDI in a well-defined ion packet thereby eliminating the need for an additional means of gating, i.e. with a Bradury-Nelson gate. Once formed, ions are made to flow by a suitable arrangement of electric fields produced by one or two easily manufactured electrodes. The ions are then separated by mobility, sampled through an aperture plate and either focused into the source region of a time-of-flight mass spectrometer to enable mass analysis of the mobility separated ions, or focused onto a conventional IMS detector to enable mobility analysis of the exiting ions. The resolution attainable with an ion mobility spectrometer is determined by a combination of the effect of a finite pulse width of originating ions and the total potential drop experienced by the ions. In one embodiment of the present invention, MALDI is the preferred ionization method and the ion packet formed is of extremely short duration (4 nanosecond laser pulse width) and composed of a limited number of ions (space charge effects on resolution are negligible). Therefore, the resolution of a MALDI/IMS spectrometer is diffusion limited and predominantly a function of the applied potential (experimentally verified by observing a constant increase in resolution with applied voltage), determined by the discharge properties of the buffer gas employed. It is an object of the present invention to maximize the sensitivity of the IMS drift cell while maintaining the resolution within the diffusion limited regime and simultaneously constructing the apparatus in a simple manner, i.e. with a minimum number of electrodes (1 or 2).

An additional advantage realized with the use of MALDI ionization is its amenability to the analysis of large molecules, particularly biologically important molecules. MALDI is a rather gentle ionization technique, thereby minimizing fragmentation of large biomolecules, particularly proteins and nucleic acids. This facilitates elucidation of sequence and structure. Analysis of such samples is simplified by minimizing fragmentation, resulting in less cluttered spectra. Other soft ionization techniques such as electrospray ionization enjoy similar advantages. When mass spectrometry is used as a detection scheme, a two dimensional pre-selection of ion is realized; one based upon simplification of ion population at the outset, and another based upon the use of mass spectrometry in addition to ion mobility.

Also described herein are instrumental improvements in the detection architecture of an ion mobility spectrometer. As used herein, the ion detector refers to any instrumental apparatus in fluid and electronic communication with the sample ionization and drift cell instrumentation and which ultimately outputs data which characterizes the sample under analysis. The ion detector may be a conventional aperture grid/collector/amplifier assembly typically used in mobility analysis. Alternatively, it may also comprise more complex instrumentation and electronics such as that which may enable mass spectrometric analysis of the chemical species separated by mobilities. In the latter case, a consistent problem with prior art instruments in throughput losses that occur in going from a high pressure stage (ion mobility drift cell) to a low pressure stage (the mass spectrometer). Instrumental modifications are described herein that represent improvements in ion throughput in comparison to conventional instruments.

Figure 16:
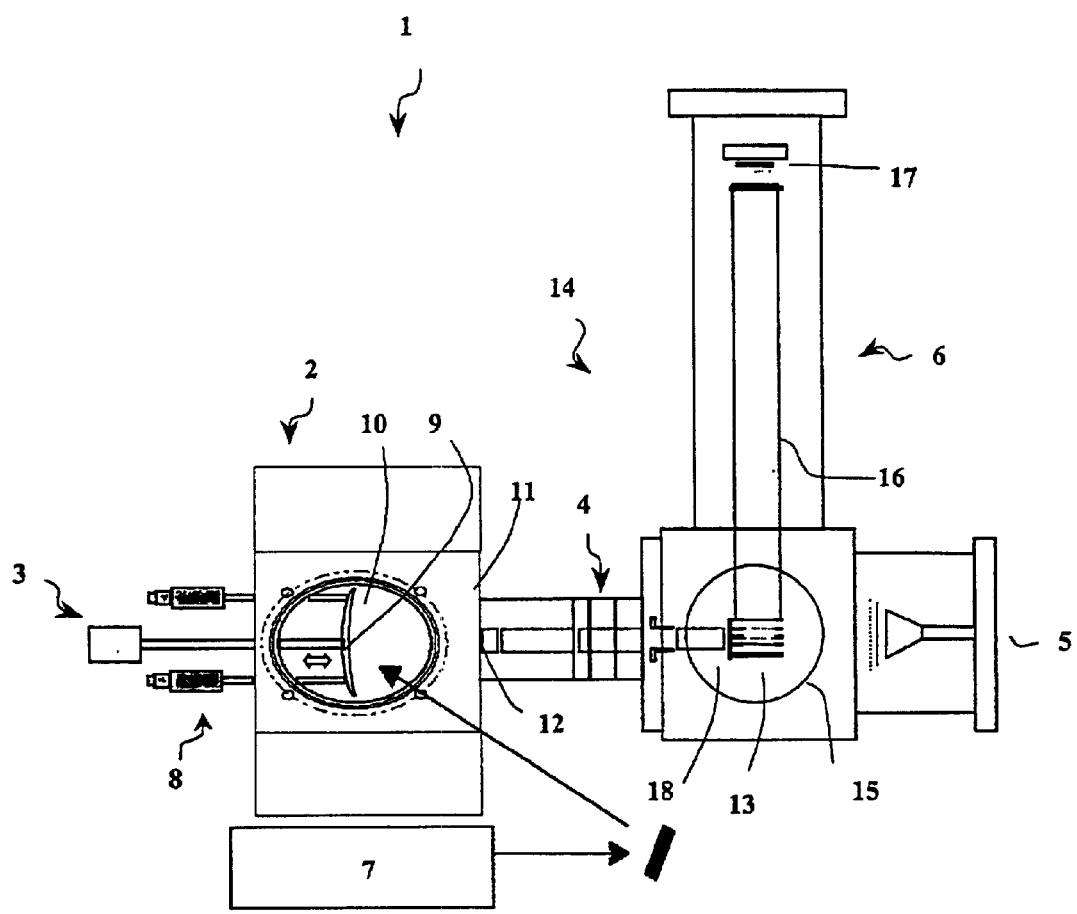
FIG. 16 is schematic view of an IMS-TOFMS spectrometer.

FIG. 16 is a schematic view of a spectrometer 1. Spectrometer 1 comprises an ion mobility cell 2, fed from an ion source 3. A lens system 4, focuses ions into a housing having a detector 5, and an orthogonal time-of-flight mass spectrometer 6. A laser 7 may be used as apart of the ion source 3 in selected applications. The laser generates gaseous molecular ions from a solid matrix/analyte sample introduced into ion mobility cell 2 through vacuum interlock 8 and deposited on probe tip or multiple well plate 9. The small packet of MALDI formed ions drift in a buffer gas under the influence of a suitable electric field applied between back electrode 10 and aperture plate 11. Following ion mobility separation in ion mobility cell 2, ions are sampled through a 200–500 micron diameter aperture 12. With a mobility cell buffer gas pressure of 1–10 Torr helium the analyzer chamber 14 is kept below $1 \times 10^{-5}$ Torr by a small high vacuum pump 15. Ions exiting aperture 12 are focused by lens system 4 onto either detector 5 to record the ion mobility arrival time distribution or into the time-of-flight source 13 where arriving ion packets are pulse focused orthogonally into a 20 cm long flight tube 16. Mass spectra are then recorded with detector 17 using normal ion counting techniques. The acquired mass spectra can either be used for m/z identification or plotted as a function of ion mobility.

Figure 17:
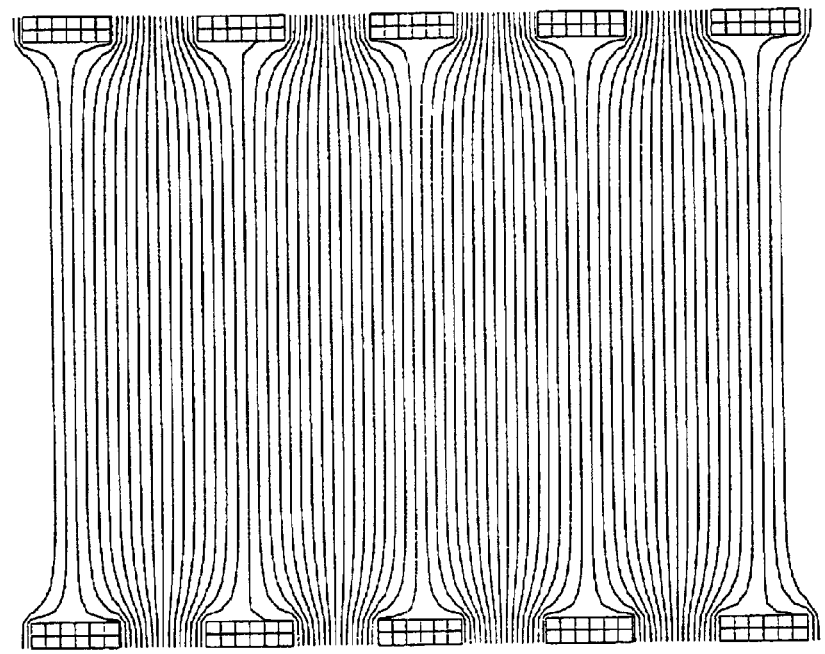
FIG. 17 is a plot of equipotential lines of typical prior art devices.
Figure 18:
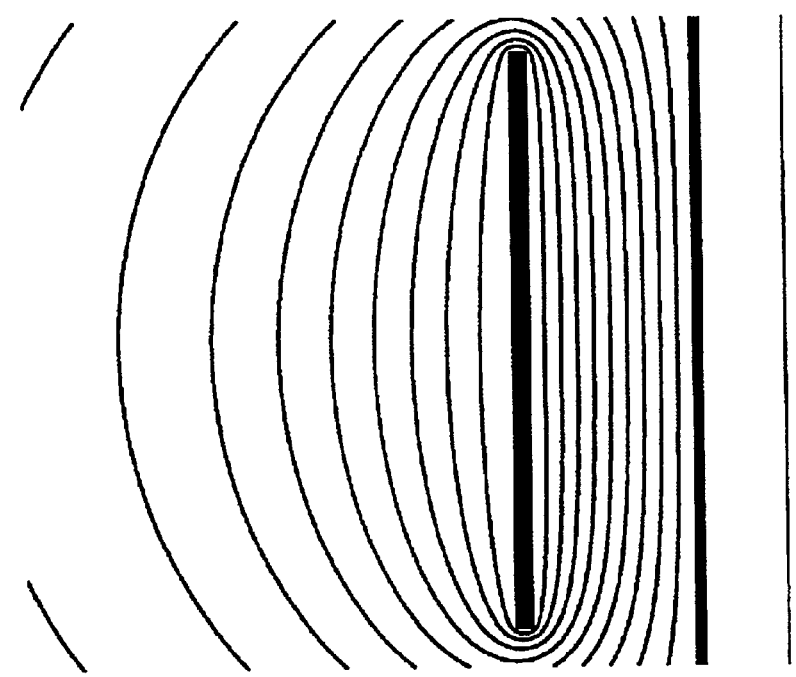
FIG. 18 is a plot of equipotential lines of a linear field produced by applying a voltage drop across two parallel discs.

FIG. 17 shows the equipotential lines of a prior art device displaying a linear electric field formed by applying a voltage across a series of equally spaced rings through a resistor chain or across a tube coated with a resistive material. The linear electric field assures that all ions experience the same field independent of radial diffusion if sampled before experiencing the fringing nonlinear fields near the side wall. In the case a of stacked ring/insulating spacer assembly several factors can degrade this ideal situation, e.g. alignment becomes critical, machining errors multiply with drift cell length, resistors must be perfectly matched, and the insulating spacers eventually degrade leading to perturbations in the linear field. It is also very difficult to coat a tube evenly with a resistive material. An alternative method to produce a linear electric field is simply to apply a voltage drop across two parallel discs as shown in FIG. 18. This method is simple but unless the discs are very large the maximum drift distance that can be used is very limited due to the non-linearity produced by fringing fields. To increase the drift distance yet maintain adequate resolution at the expense of field linearity a radius of curvature has been added to the electrode yielding focusing properties to increase the drift cell sensitivity.

Radius of Curvature Electrode

Figure 19:
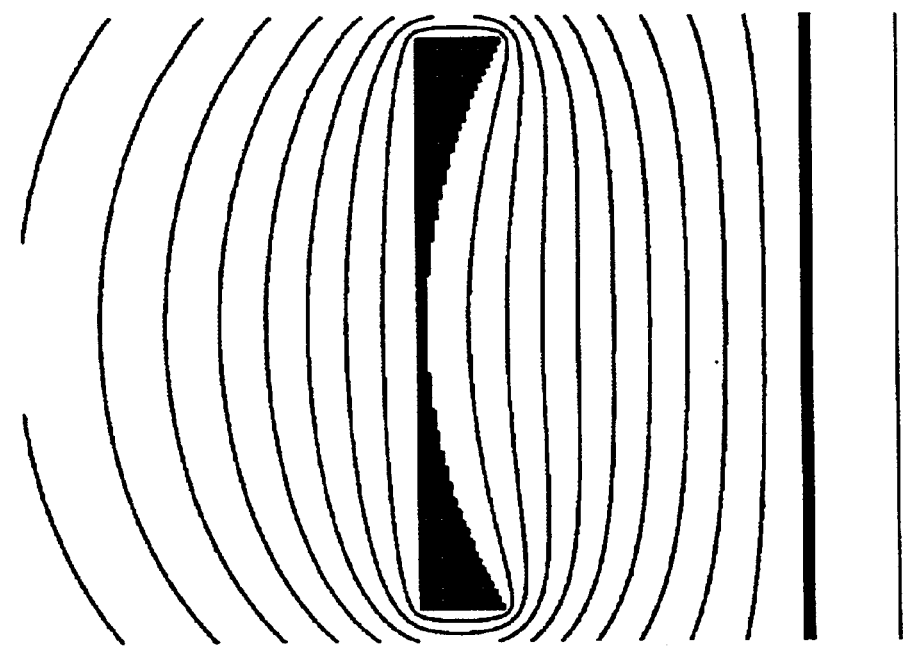
FIG. 19 illustrates the equipotential lines obtained using a radius of curvature electrode and a flat disc electrode.

FIG. 19 shows the equipotential lines formed between an electrode with a 6" radius of curvature and a grounded flat plate. Note that the region of linearity may be lengthened by using a vacuum can of insulating material, e.g. glass or plastic in which case the penetrating fields are eliminated. This embodiment of the present invention is easy to manufacture and assemble, and is very robust. The drift cell interior is accessible by removing the top view port for cleaning resulting in short down times between experiments. The device also provides moderate resolution (20–40) and high sensitivity (10 femtomoles of loaded sample).

Field Correcting Ring Electrode

Figure 20:
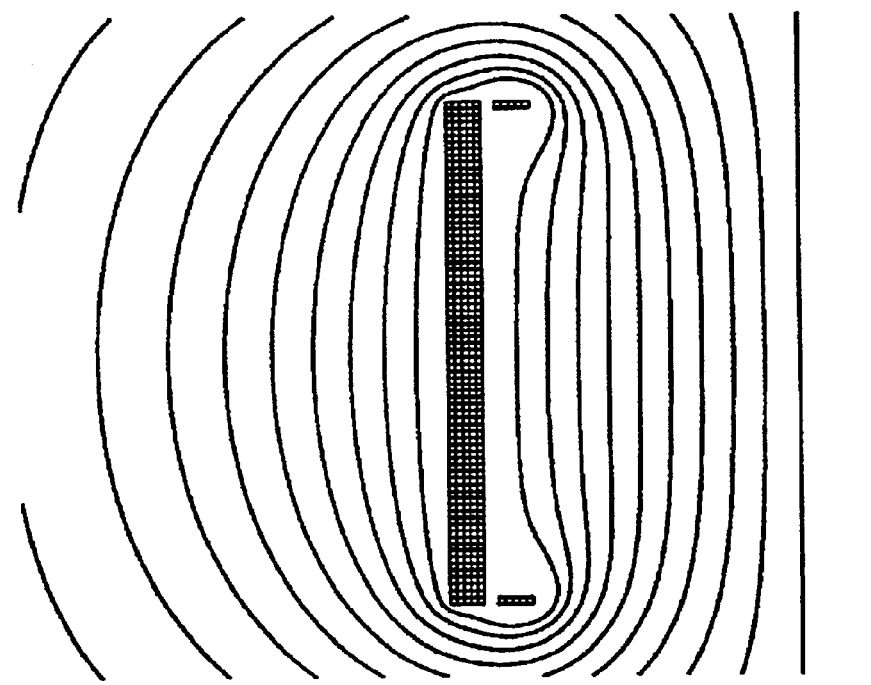
FIG. 20 illustrates the equipotential lines obtained using a field correcting ring and a flat disc electrode.

FIG. 20 illustrates the equipotential lines in an embodiment of the present invention having a field correcting ring in addition to flat disc electrode. A device so configured can be adjusted to produce an interior electric field ranging from linear to highly non-linear and all combinations between.

Flat Disc with Second Movable Cylindrical Electrode

Figure 21:
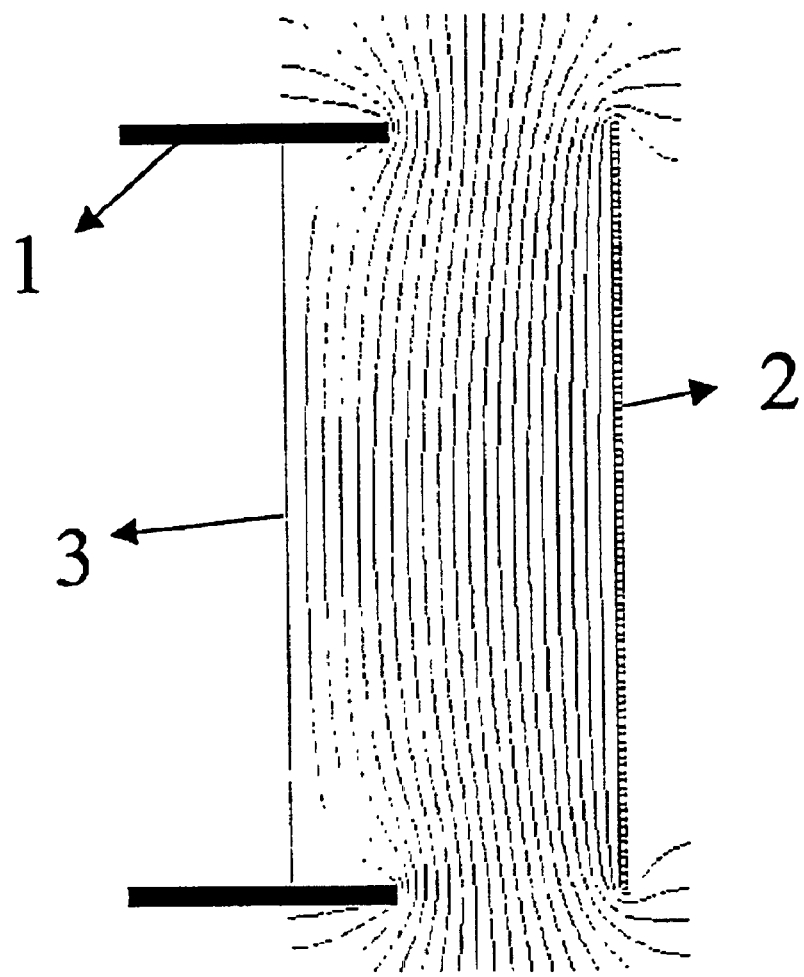
FIG. 21 illustrates the equipotential lines in another embodiment having a flat electrode and a second movable electrode.

FIG. 21 illustrates the equipotential lines in another embodiment having a flat electrode and a second movable electrode. Such a device can be adjusted to produce and interior electric field ranging from linear to highly non-linear and a continuous range of combinations in between.

RF Focusing Interface

Figure 22:
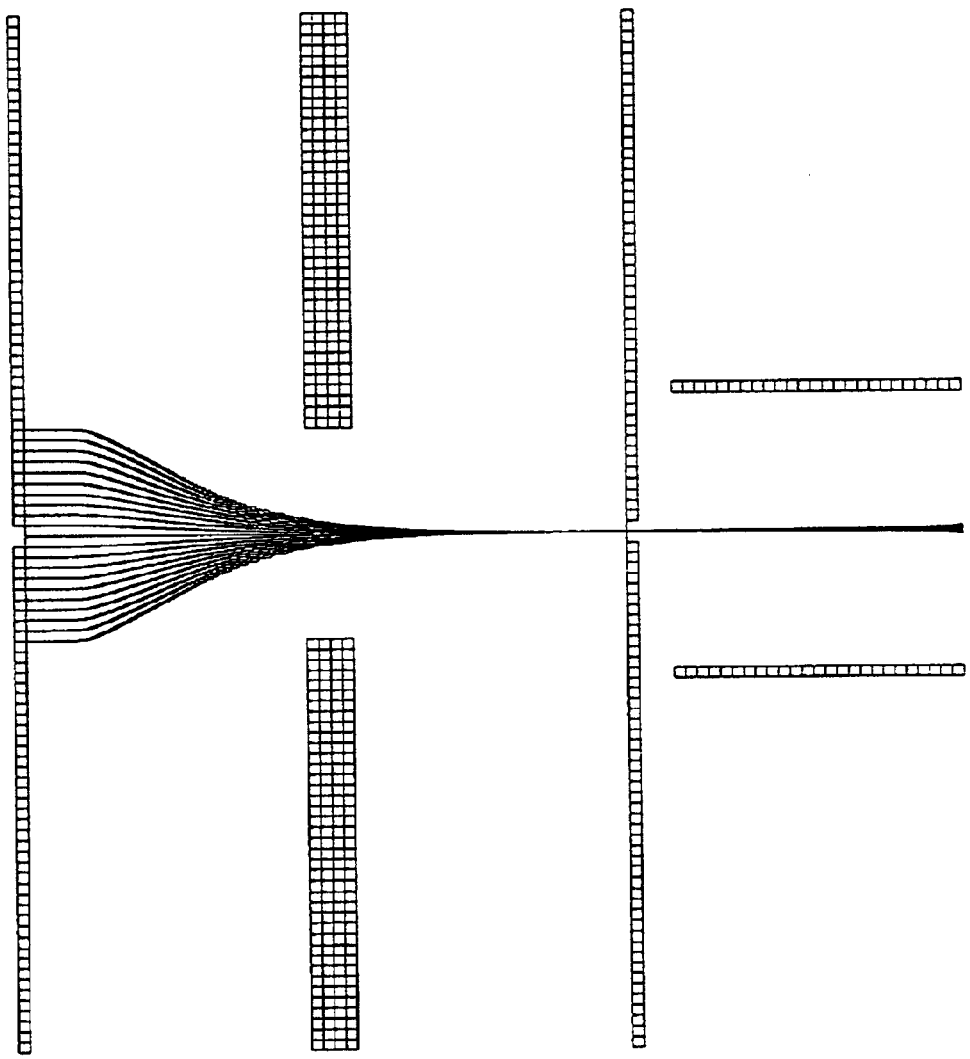
FIG. 22 illustrate the performance of a device using the rf focusing interface embodiment of the invention.

The embodiment of the present invention as depicted in FIG. 16 is limited to a drift/buffer gas pressure of 1–50 Torr due to a single stage of pumping on the ion detector and mass spectrometer. A higher operating buffer gas pressure allows for a higher electrode voltage and subsequent higher resolution. To maintain a collision free vacuum in the analyzer chamber at higher drift cell pressures requires either the use of larger vacuum pumps or an additional stage of differential pumping. But a standard interface operating at ca. 1 Torr would compromise the sensitivity of the apparatus due to excessive ion losses. Several reported attempts have been made to increase the ion transmission in an interface region. Smith et al. implemented an ion funnel (PCT WO 97/49111), consisting of a series of decreasing diameter ring electrodes to which an alternating RF voltage and linear DC voltage is applied. Krutchinsky et al. used a segmented RF only quadrupole (Proceedings of the 43rd ASMS Conference, 1995, 126). Both could increase the ion transmission significantly. It is a further object of the present invention to provide a simple, yet highly efficient ion interface to transport ions through an intermediate region between a high background pressure device and a high vacuum device. Without compromising the small scale dimensions of the apparatus an alternative embodiment comprising a radio frequency focusing interface. In this embodiment, ions exiting aperture 12 (see FIG. 16) encounter a combination of a RF electric field and a DC electric field in the presence of buffer gas collisions. The resulting ion trajectories are shown in FIG. 22, illustrating the superb focusing characteristics of this device.

Microchannel Plate Aperture

Figure 23:
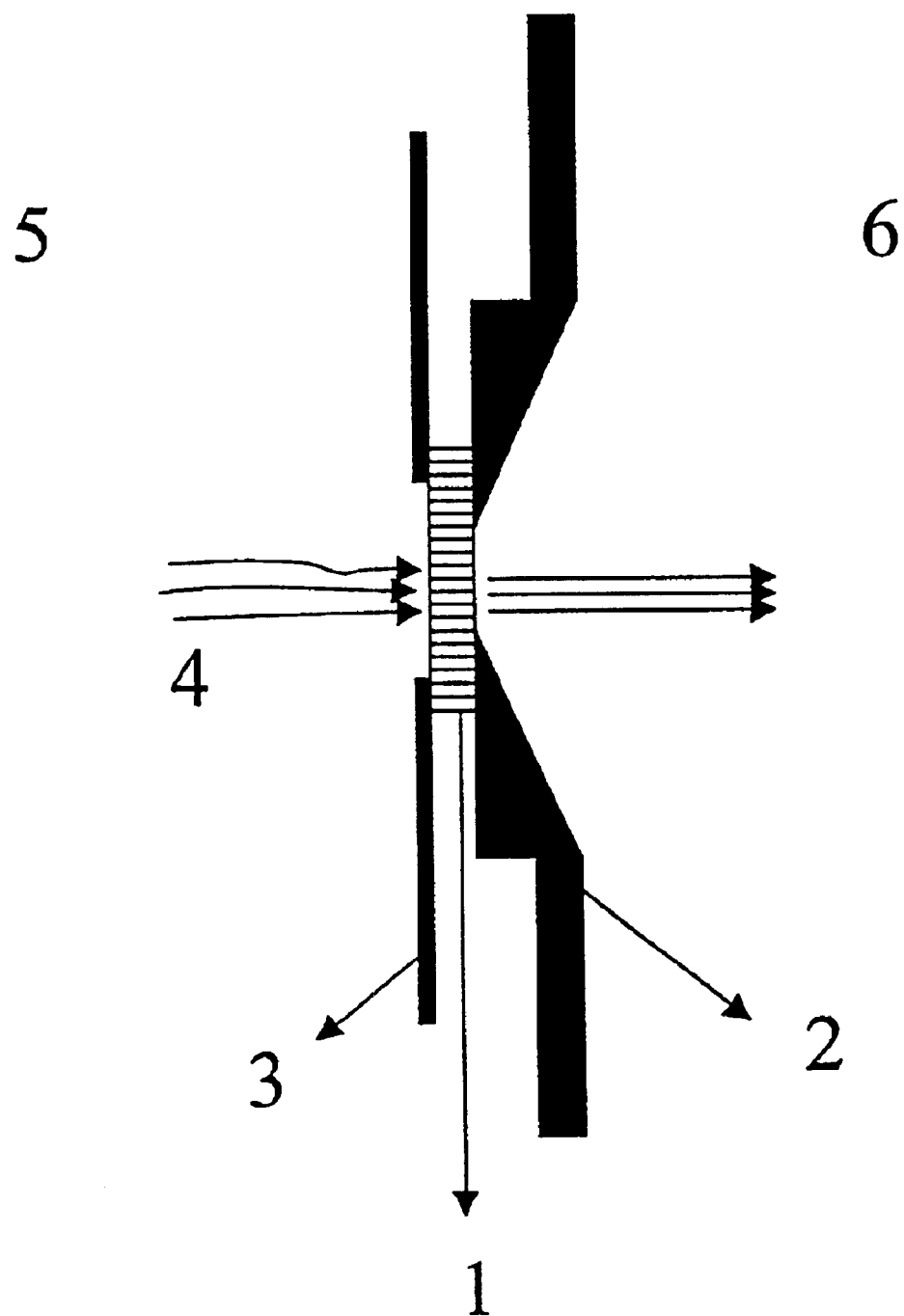
FIG. 23 illustrates the microchannel plate aperture embodiment of the present invention.

FIG. 23 shows a schematic of an alternative embodiment of one section of the present invention comprising the aperture plate by which ions are sampled. The mobility chamber 5 at high pressure is separated from the analyzer chamber 6 at vacuum by a multi-capillary interface, e.g. a microchannel plate 1. High ion transmission can be achieved by reverse biasing a semi-conductive capillary in the presence of gas flow and a temperature gradient as described in U.S. Pat. No. 5,736,740 to Franzen. The preferred embodiment of the present invention utilizes a bundle of capillaries acting as a pressure stop and ion interface to reduce the vacuum pump requirements. The optimum diameter to length ratio will depend on the required pressure drop as well as on the absolute pressure. The diameter of the microchannel interface can be much larger than a single aperture thereby transmitting ions that diffuse in the radial direction in the drift chamber that would otherwise be lost.

Mobility/MS/MS

A further alternate embodiment of the present invention comprises pre-selecting parent ions by their mobility for fragmentation. The form of fragmentation includes in part, methods known in the art such as collision-induced dissociation (CID), surface-induced dissociation (SID), electron impact or photo-induced dissociation with the preferred method of dissociation being SID. In FIG. 16, the SID surface 18 is located between lens system 4 and time-of-flight source 13 and preferably is comprised of a rotatable fine mesh grid. The advantage of the present invention embodiment is the simultaneous detection of parent and fragment ions: fragment ions will appear at the same mobility time as the parent ions without scanning the entire mass range at a specific mobility drift time. To eliminate any energy differences between the parent and fragment ions that occur during the dissociation process a RF focusing quadrupole onto which a linear electric field in superimposed is located behind the SID) grid. All ions are cooled by collisions in the RF quadrupole and therefore arrive at the time-of-flight source simultaneously. Because higher energy collisions in CID result in a greater degree of fragmentation, the collision energy may be increased by using an electric field to accelerate the ions within the expanding gas flow during transmission from the ion mobility drift cell to the mass spectrometer.

Performance

Figures 24, 25:
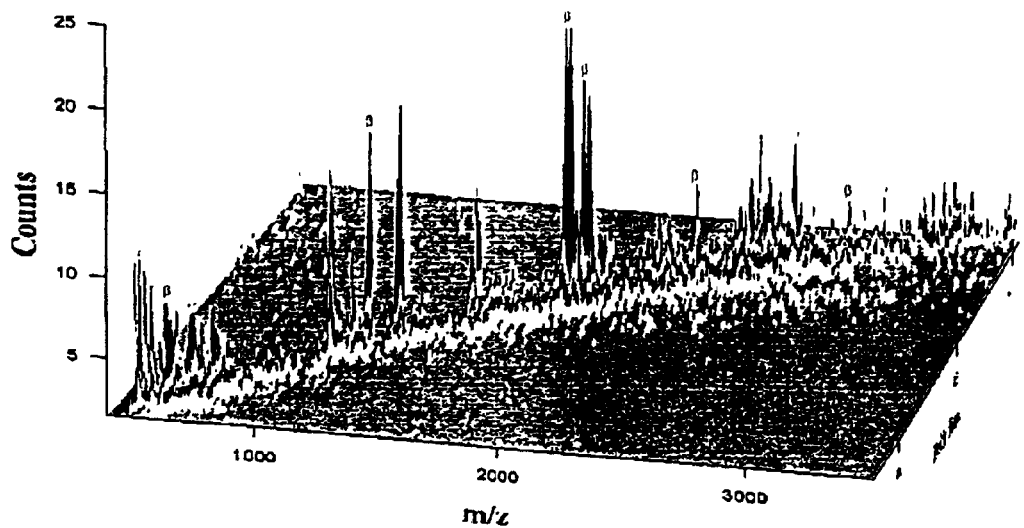
FIG. 24 a three-dimensional plot of mass spectra of a two component mixture of bovine hemoglobin $\alpha$ and $\beta$ analyzed using the present invention with a high resolution TOFMS.
FIG. 25 gives tabulated data results for the experiment of FIG. 24.

One of the many applications of the apparatus is in the field of proteomics, specifically protein mixture analysis. Current analytical techniques are time consuming and labor intensive but a gas phase separation method such as ion mobility spectrometry is more congruous with mass analysis so by combining the separation step and the mass analysis into a single instrument as in the present invention the throughput of the system is greatly increased. Also, the present invention displays increased sensitivity in the analysis of protein mixtures over a typical MALDI time-of-flight mass spectrometry experiment. To compare the two methods a two component mixture consisting of a tryptic digest of bovine hemoglobin $\alpha$ and $\beta$ was analyzed on the apparatus of the present invention and on a state of the art high resolution time-of-flight mass spectrometer. The ion mobility experiment, for which the 3-dimensional plot of mass spectra is shown in FIG. 24, observed a greater percentage of the total amino acids present in the sample relative to the optimized MALDI-TOF protocol (94% amino acid coverage for both hemoglobin $\alpha$ and $\beta$ versus 75% and 68% on the MALDI-TOF instrument). The observed increase in % coverage is attributed to the increased sensitivity of the present invention. As a further test a more complex mixture consisting of horse heart cytochrome c, chicken egg white lysozyme, bovine serum albumin, bovine hemoglobin $\alpha$ and bovine hemoglobin $\beta$ was used. The same sample was analyzed using optimized sample preparation procedures on both the apparatus of the present invention and the MALDI-TOF instrument. The table shown in FIG. 25 clearly illustrates that the apparatus of the present invention yields higher overall % amino acid coverage and individual % amino acid coverage for a complex protein mixture. In addition, the apparatus of the present invention demonstrates higher sensitivity toward lysine terminated digest fragments. (Krause, E. et al. Anal. Chem. 1999, 71, 4160–4165). This phenomenon is typified in the case of cytochrome c, for which both experiments result in 60% of the total predicted arginine terminated fragments being observed, but the experiment using the apparatus of the present invention results in the observation of a much greater percentage of the lysine terminated fragments (52% versus 16%). The results suggest that performing MALDI/on Mobility/Mass analysis of protein mixtures where ions are formed in a low pressure environment (is this case 5 Torr helium) involves a different desorption process than when ions are formed by MALDI in a high vacuum environment. This statement is further supported by a comparison of spectra obtained in the two environments. If the same digest sample is analyzed with the high vacuum instrument using the same matrix and sample preparation as with the apparatus of the present invention the % coverage for a protein digest or a digest of a complex protein mixture is extremely low and only a few fragments are identifiable.

Therefore, further objects of the present invention include simplification, increased throughput, increased overall sensitivity, and increased sensitivity toward lysine terminated digest fragments present in complex mixtures.

REFERENCES

All patents and publications mentioned in the specification are indicative of the level of those skilled in the art to which the invention pertains. All patents and publications are herein incorporated by reference to the same extent as if each individual publication was specifically and individually indicated to be incorporated by reference.

Barnes, D. W. et al., *Phys. Rev. Lett.*, 1961, 6, 110.

Septier, A. (Editor), Focusing of Charged Particles, Academic Press, (1967) 267–247.

Young, C. E. et al., *J. Chem. Phys.*, 1970, 53, 4295.

Gillig, K. J. et al., *Proceedings of the 44th ASMS Conference*, 1996, Portland, Oreg., p. 1168.

Gillig, K. J., "The Development of a Fourier Transform Ion Cyclotron Resonance Ion Mobility Spectrometer and Studies of Ion Motion in a Wiere Ion Guide Cell", Texas A&M University, Dissertation 1997.

Guan, S.; Marshall, A., *J. Am. Soc. Mass Spectrom.*, 1996, 7, 101–106.

Livingston, M. S.; Blewett, J. P., "Particle Accelerators", pp. 584–595, McGraw-Hill Book Co., Inc., 1962.

Eiceman, G. A.; Karpas, Z., "Ion Mobility Spectrometry", CRC Press, Inc. 1994.

Mason, E. A.; McDaniel, E. W., "The Mobility and Diffusion of Ions in Gases", pp. 68–72, J. Wiley & Sons, 1973.

Gatland, I. R., "Case Studies in Atomic Physics IV", McDaniel, E. W., McDowell, M. R. C., Ed., North Holland Publishing Company: Amsterdam, 1975, p. 371.

Krutchinsky et al. *Proceedings of the 43rd ASMS Conference*, 1995, 126.

Krause, E. et al. *Anal. Chem.*, 1999, 71, 4160–4165.

McKight, et al. *Phys. Rev.*, 1967, 164, 62.

Shoff, D. B.; Harden, C. S. *Anal. Chem.* 1997, 1(5) 285–294.

One skilled in the art readily appreciates that the present invention is well adapted to carry out the objectives and obtain the ends and advantages mentioned as well as those inherent therein. Systems, methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the claims.

What is claimed is:

1. An apparatus for separating and analyzing ions, comprising:

an ionization source to generate ions, an ion drift cell coupled to said ionization source, in which the ions are separated according to their mobility and which comprises electrodes for transporting and focusing the ions, said focusing comprises a superposition of periodic field focusing and hyperbolic field focusing; and, a detector coupled to said ion drift cell to detect the ions.

2. The apparatus of claim 1 wherein said detector is a mass spectrometer.

3. The apparatus of claim 2 wherein said mass spectrometer is coupled to said ion drift cell by a microchannel aperture plate comprising a bundle of capillaries.

4. The apparatus of claim 3 wherein a voltage is applied across said microchannel aperture plate.

5. The apparatus of claim 3 wherein said capillaries are of increasing diameter, having the larger diameter capillaries facing the mobility drift cell.

6. The apparatus of claim 2 further comprising a radio frequency focusing interface between said drift cell and said ion detector.

7. The apparatus of claim 6 wherein said radio frequency focusing interface comprises a combination of a radio frequency electric field and a direct current electric field.

8. The apparatus of claim 2 wherein said mass spectrometer is a time-of-flight mass spectrometer having a flight tube positioned orthogonally with respect to the ion drift cell axis.

9. The apparatus of claim 2 further comprising means for fragmenting ions, said means for fragmenting being coupled to said ion drift cell to receive ions therefrom, and positioned prior to said mass spectrometer.

10. The apparatus of claim 9 wherein said means for fragmenting ions comprises collisions of said ions with gas particles.

11. The apparatus of claim 10 wherein said collisions occur in the expanding gas flow during the transmission of ions from said drift cell to said mass spectrometer.

12. The apparatus of claim 11 wherein the collision energy of said collisions may be increased by accelerating the ions in an electrical field within said expanding gas flow.

13. The apparatus of claim 9 wherein said means for fragmenting ions comprises electron impact fragmentation.

14. The apparatus of claim 9 wherein said means for fragmenting ions comprises surface induced dissociation.

15. The apparatus of claim 9 further comprising a radio frequency quadrupole.

16. The apparatus of claim 1 wherein said electrodes are comprised of regions of conical shape.

17. The apparatus of claim 1 wherein said electrodes comprise thick plate electrodes possessing a central hole wherein said central hole has a conical shape.

18. The apparatus of claim 1 wherein said electrodes have unequal potential differences applied between them.

19. The apparatus of claim 1 wherein said electrodes comprise electrodes with unequal hole diameters.

20. The apparatus of claim 1 wherein said electrodes comprise electrodes having unequal spacing between them.

21. The apparatus of claim 1 wherein said electrodes comprise cup-shaped electrodes.

22. The apparatus of claim 1 wherein said ion drift cell comprises a stack of electrodes with insulating material between the electrodes.

23. The apparatus of claim 22 further comprising seal rings in said stack in order to seal said drift section.

24. The apparatus of claim 22 further comprising positioning rings in order to position said electrodes along the axis of said drift chamber.

25. The apparatus of claim 22 further comprising a positioning tube in order to position said electrodes along the axis of said drift chamber.

26. The apparatus of claim 25 wherein said positioning tube also seals said drift chamber.

27. The apparatus of claim 1 wherein said ionization source to generate ions comprises:

an ionizing beam; and, a sample holder with a surface to accommodate a sample to receive said ionizing beam.

28. The apparatus of claim 27 further comprising one or more mirrors positioned to redirect said ionizing beam onto said surface so that said ionizing beam can enter from behind said surface.

29. The apparatus of claim 27 further comprising one or more mirrors positioned to redirect said ionizing beam onto said surface so that said ionizing beam can enter said drift chamber essentially orthogonally to its axis.

30. The apparatus of claim 27 wherein said sample holder comprises a sample holder allowing sequential exposure of several samples to the ionizing beam.

31. The apparatus of claim 30 wherein said sample holder comprises a rotatable sample holder.

32. The apparatus of claim 30 wherein said sample holder is positioned orthogonally to an ion mobility drift cell.

33. The apparatus of claim 30 wherein said sequential exposure of said samples comprises the use of a moving belt to carry said samples to the position of said ionizing beam.

34. The apparatus of claim 1 where said electrodes each accommodate several openings in order to transport and focus several parallel beams of ions.

35. An apparatus for transporting ions, comprising:

an ion drift cell, which comprises electrodes for transporting and focusing the ions, said focusing consisting of a superposition of periodic field focusing and hyperbolic field focusing.

36. An apparatus for transporting ions, comprising:

an ion drift cell, which comprises electrodes for transporting and focusing the ions, said focusing consisting of a combination of periodic field focusing and hyperbolic field focusing.

37. An apparatus for separating and analyzing ions, comprising:

an ionization source to generate ions, an ion drift cell coupled to said ionization source, in which the ions are separated according to their mobility and which comprises sliding tube electrodes for focusing the ions, wherein said focusing comprises hyperbolic field focusing; and, a detector coupled to said ion drift cell to detect the ions.

38. The apparatus of claim 37 wherein said electrodes comprise an electrode of hyperbolic shape.

39. An apparatus for separating and analyzing ions, comprising:

an ionization source to generate ions, an ion drift cell coupled to said ionization source, in which the ions are separated according to their mobility and which comprises electrodes for focusing the ions, said focusing consisting of a combination of periodic field focusing and hyperbolic field focusing; and, a detector coupled to said ion drift cell to detect the ions.

40. The apparatus of claim 39 wherein said combination consists essentially of a sequential combination of a periodic focusing field and a hyperbolic focusing field.

41. A method for separating and analyzing ions, comprising:

generating ions from an ion source, separating ions in terms of their mobility wherein said step of separating comprises transporting the ions in a superposition of a periodic focusing field and a hyperbolic focusing field; and, detecting said ions.

42. The method of claim 41 wherein said step of detecting comprises detecting with a mass spectrometer.

43. The method of claim 42 wherein said step of detecting with a mass spectrometer comprises detecting with a time-of-flight mass spectrometer having a flight tube positioned orthogonally with respect to the ion drift cell axis.

44. The method of claim 43 further comprising the step of fragmenting ions after the mobility separation and prior to said detecting with a mass spectrometer.

45. The method of claim 44 wherein said step of fragmenting ions comprises fragmenting ions by collisions of said ions with gas particles.

46. The method of claim 44 wherein said step of fragmenting ions comprises collisions occurring in an expanding gas flow during the transmission of said drift cell with said mass spectrometer.

47. The method of claim 46 further comprising increasing the collision energy of said ions with said gas particles by accelerating the ions in an electrical field within said expanding gas flow.

48. The method of claim 41 wherein said step of transporting comprises focusing with ring electrodes of conical shape.

49. The method of claim 41 wherein said step of transporting comprises focusing with thick plate ring electrodes beveled to possess a central hole wherein said central hole has a conical shape.

50. The method of claim 41 wherein said step of transporting comprises focusing in which unequal potential differences are applied between the electrodes.

51. The method of claim 41 wherein said step of transporting comprises focusing using electrodes with unequal hole diameters.

52. The method of claim 41 wherein said step of transporting comprises focusing by unequal spacing between the electrodes.

53. The method of claim 41 wherein said step of transporting comprises focusing by cup-shaped electrodes.

54. The method of claim 41 wherein said step of separating comprises separating using a stack of electrodes with insulating material between those electrodes.

55. The method of claim 54 further comprising sealing said stack with sealing rings in order to seal said drift section.

56. The method of claim 54 further comprising positioning said electrodes along the axis of said drift chamber using positioning rings.

57. The method of claim 54 further comprising positioning said electrodes along the axis of said drift chamber using a positioning tube.

58. The method of claim 57 wherein said positioning also seals said drift chamber.

59. The method of claim 41 wherein said step of generating ions comprises:
ionizing sample using an ionizing beam directed to the sample positioned on a sample holder, said sample holder having a surface to accommodate a sample to receive said ionizing beam.

60. The method of claim 59 further comprising the step of redirecting said ionizing beam onto said surface using one or more mirrors positioned to so that said ionizing beam can enter from behind said surface.

61. The method of claim 59 further comprising the step of redirecting said ionizing beam onto said surfaces using one or more mirrors positioned so that said ionizing beam can enter said drift chamber essentially orthogonally to the drift chamber axis.

62. The method of claim 59 further comprising the step of sequentially exposing several samples to the ionizing beam.

63. The method of claim 62 where said step of sequentially exposing comprises rotating said sample holder.

64. The method of claim 62 where said step of sequentially exposing comprises moving said sample holder to a position orthogonal to the axis of said drift cell.

65. The method of claim 62 where said step of sequentially exposing said samples comprises using a moving belt to deliver said samples.

66. A method for separating and analyzing ions, comprising:
generating ions from an ion source,
separating ions in terms of their mobility wherein said step of separating comprises transporting the ions in a hyperbolic focusing field wherein said field is generated by electrodes comprising a sliding tube electrode or an electrode of hyperbolic shape; and,
detecting said ions.

67. A method for separating and analyzing ions, comprising:
generating ions from an ion source,
separating ions in terms of their mobility wherein said step of separating comprises transporting the ions in a combination of a periodic focusing field and a hyperbolic focusing field; and,
detecting said ions.

68. The method of claim 67 wherein said combination essentially consists of serially applying the periodic field focusing and the hyperbolic field focusing.

69. An apparatus for performing ion mobility spectrometry comprising:
an ionization source;
a drift cell, fluidly coupled to said ionization source, said drift cell to receive ions from said ionization source and having an electrode assembly comprising components selected from the group consisting of at least one field correcting ring electrode and at least one movable cylindrical electrode, wherein said electrode assembly is a parallel electrode assembly when said assembly comprises at least two components; and,
an ion detector, fluidly coupled to said drift cell, said ion detector to receive and detect ions from said drift cell.

70. The apparatus of claim 69 wherein said ionization source is a matrix assisted laser desorption ionization source.

71. The apparatus of claim 69 wherein said ionization source is selected from the group consisting of an electrospray ionization apparatus, a laser ionization apparatus, a photoionization apparatus, an electron ionization apparatus, a chemical ionization apparatus, an electric field ionization apparatus, a surface ionization apparatus, a radioactive ionization apparatus, a discharge ionization apparatus; and, a multiphoton ionization apparatus.

72. The apparatus of claim 69 wherein said ion detector is selected from the group consisting of an ion collector with an amplifier, and a mass spectrometer.

73. The apparatus of claim 72 wherein said ion detector is a time-of-flight mass spectrometer.

74. The apparatus of claim 73 wherein the axis defined by said drift cell is perpendicular to the axis defined by said flight tube of the time-of-flight mass spectrometer.

75. The apparatus of claim 73 wherein said time-of-flight ion source comprises a collision-induced dissociation apparatus.

76. The apparatus of claim 73 wherein said time-of-flight ion source comprises a surface-induced dissociation apparatus.

77. The apparatus of claim 73 wherein said time-of-flight ion source comprises a photo-induced dissociation apparatus.

78. The apparatus of claim 69 further comprising a microchannel aperture plate between said drift cell and said ion detector.

79. The apparatus of claim 78 wherein said microchannel aperture plate comprises a bundle of capillaries.

80. The apparatus of claim 69 further comprising a radio frequency focusing interface between said drift cell and said ion detector.

81. The apparatus of claim 80 wherein said radio frequency focusing interface comprises a combination of a radio frequency electric field and a direct current electric field.

82. An apparatus for performing ion mobility spectrometry
comprising:
an ionization source;
a drift cell, fluidly coupled to said ionization source, said drift cell to receive ions from said ionization source and having an electrode assembly comprising at least one radius of curvature electrode wherein the radius of curvature is collinear with the separation axis of the drift cell, wherein said electrode assembly is a parallel electrode assembly when said assembly comprises at least two components; and,
an ion detector, fluidly coupled to said drift cell, said ion detector to receive and detect ions from said drift cell.

83. The apparatus of claim 82 wherein said ionization source is a matrix assisted laser desorption ionization source.

84. The apparatus of claim 82 wherein said ionization source is selected from the group consisting of an electrospray ionization apparatus, a laser ionization apparatus, a photoionization apparatus, an electron ionization apparatus, a chemical ionization apparatus, an electric field ionization apparatus, a surface ionization apparatus, a radioactive ionization apparatus, a discharge ionization apparatus; and, a multiphoton ionization apparatus.

85. The apparatus of claim 82 wherein said ion detector is selected from the group consisting of an ion collector with an amplifier, and a mass spectrometer.

86. The apparatus of claim 85 wherein said ion detector is a time-of-flight mass spectrometer.

87. The apparatus of claim 86 wherein the axis defined by said drift cell is perpendicular to the axis defined by said flight tube of the time-of-flight mass spectrometer.

88. The apparatus of claim 87 wherein said time-of-flight ion source comprises a collision-induced dissociation apparatus.

89. The apparatus of claim 87 wherein said time-of-flight ion source comprises a surface-induced dissociation apparatus.

90. The apparatus of claim 87 wherein said time-of-flight ion source comprises a photo-induced dissociation apparatus.

91. The apparatus of claim 82 further comprising a microchannel aperture plate between said drift cell and said ion detector.

92. The apparatus of claim 91 wherein said microchannel aperture plate comprises a bundle of capillaries.

93. The apparatus of claim 82 further comprising a radio frequency focusing interface between said drift cell and said ion detector.

94. The apparatus of claim 93 wherein said radio frequency focusing interface comprises a combination of a radio frequency electric field and a direct current electric field.

95. A method of collecting ion mobility spectrometric information comprising:
generating a gaseous sample of ions using a technique selected from the group consisting of:
matrix assisted laser desorption ionization, electrospray ionization, laser ionization, photoionization, an electron ionization, chemical ionization, electric field ionization, surface ionization, radioactive ionization, discharge ionization; and, multiphoton ionization,
separating said gaseous sample of ions into packets of ions according to the ion mobilities of said packets through use of a drift cell having an electrode assembly comprising components selected from the group consisting of at least one field correcting ring electrode and at least one movable cylindrical electrode, wherein said electrode assembly is a parallel electrode assembly when said assembly comprises at least two components; and,
detecting said ion packets.

96. The method of claim 95 wherein said step of detecting ion packets comprises the use of and ion collector and an amplifier.

97. The method of claim 95 wherein said step of detecting ion packets comprises the use of a system comprising a mass spectrometer.

98. The method of claim 95 wherein said step of detecting ion packets comprises the use of a system comprising a time-of-flight mass spectrometer.

99. The method of claim 98 wherein said step of detecting ion packets further comprises pre-selecting parent ions by a step selected from the group consisting of collision-induced dissociation, photo-induced dissociation; and surface-induced dissociation.

100. The method of claim 99 wherein said step of pre-selecting parent ions further comprises focusing said parent ions and any fragment ions using a radio frequency quadrupole.

101. A method of collecting ion mobility spectrometric information comprising:
generating a gaseous sample of ions using a technique selected from the group consisting of:
matrix assisted laser desorption ionization, electrospray ionization, laser ionization, photoionization, an electron ionization, chemical ionization, electric field ionization, surface ionization, radioactive ionization, discharge ionization; and, multiphoton ionization,
separating said gaseous sample of ions into packets of ions according to the ion mobilities of said packets through use of a drift cell having an electrode assembly comprising at least one radius of curvature electrode, wherein said electrode assembly is a parallel electrode assembly when said assembly comprises at least two components; and,
detecting said ion packets.

102. The method of claim 101 wherein said step of detecting ion packets comprises the use of and ion collector and an amplifier.

103. The method of claim 101 wherein said step of detecting ion packets comprises the use of a system comprising a mass spectrometer.

104. The method of claim 102 wherein said step of detecting ion packets comprises the use of a system comprising a time-of-flight mass spectrometer.

105. The method of claim 104 wherein said step of detecting ion packets further comprises pre-selecting parent ions by a step selected from the group consisting of collision-induced dissociation, photo-induced dissociation; and surface-induced dissociation.

106. The method of claim 105 wherein said step of pre-selecting parent ions further comprises focusing said parent ions and any fragment ions using a radio frequency quadrupole.

* * * * *